(12) United States Patent
Mercolino

(10) Patent No.: US 8,247,018 B2
(45) Date of Patent: Aug. 21, 2012

(54) METHODS FOR QUALITY CONTROL

(75) Inventor: Thomas J. Mercolino, Stockton, NJ (US)

(73) Assignee: Authentiform Technologies, LLC, Chapel Hill, NC (US)

( * ) Notice: Subject to any disclaimer, the term of this patent is extended or adjusted under 35 U.S.C. 154(b) by 1325 days.

(21) Appl. No.: 11/613,437

(22) Filed: Dec. 20, 2006

(65) Prior Publication Data

US 2007/0160814 A1 Jul. 12, 2007

Related U.S. Application Data

(63) Continuation-in-part of application No. 11/455,817, filed on Jun. 20, 2006.

(60) Provisional application No. 60/692,225, filed on Jun. 20, 2005.

(51) Int. Cl.
*A61L 33/00* (2006.01)

(52) U.S. Cl. .............. 427/2.1; 235/462.01; 235/462.25; 235/462.1; 235/462.11; 235/462.16; 250/302; 427/411; 427/8; 427/212; 700/225; 215/232

(58) Field of Classification Search .................. 250/302, 250/556, 483.1, 492.1; 235/462.01, 462.1, 235/462.11, 462.16, 462.25, 375; 215/232; 700/225; 229/3.5; 436/524; 382/115
See application file for complete search history.

(56) References Cited

U.S. PATENT DOCUMENTS

| | | | |
|---|---|---|---|
| 1,787,995 A | 1/1931 | Reilly | |
| 3,861,886 A | 1/1975 | Meloy | |
| 4,053,433 A | 10/1977 | Lee | |
| 4,250,382 A * | 2/1981 | Libby | ............... 250/302 |
| 4,267,234 A | 5/1981 | Rembaum | |
| 4,267,235 A | 5/1981 | Rembaum et al. | |
| 4,345,604 A | 8/1982 | Renirie | |
| 4,423,819 A * | 1/1984 | Cummings | ............... 215/232 |
| 4,552,812 A | 11/1985 | Margel et al. | |
| 4,640,035 A | 2/1987 | Kind et al. | |
| 4,677,138 A | 6/1987 | Margel | |
| 4,767,205 A | 8/1988 | Schwartz et al. | |
| 5,139,812 A | 8/1992 | Lebacq | |
| 5,289,547 A | 2/1994 | Ligas et al. | |
| 5,429,952 A | 7/1995 | Garner et al. | |
| 5,450,190 A | 9/1995 | Schwartz et al. | |

(Continued)

FOREIGN PATENT DOCUMENTS

DE 103 45 458 A1 10/2004

(Continued)

OTHER PUBLICATIONS

Hobby Industry Technology Site, Manufacturers Guide to Bar Code Common Forms and EC/EDI, May 2001, pp. 1-4.*

(Continued)

*Primary Examiner* — Dah-Wei Yuan
*Assistant Examiner* — Andrew Bowman
(74) *Attorney, Agent, or Firm* — Deborah Hill Spencer; Andrew Gerschutz; Moore & Van Allen, PLLC

(57) ABSTRACT

The present invention relates to method for quality control of surface coated objects used independently or in conjunction with product authentication; methods for assuring proper product handling; methods for assuring that product contents' match product's label, comprising the use of microparticulate taggants having different detectable physical properties, wherein each combination of properties is used as an encoding bit to create codes.

76 Claims, 6 Drawing Sheets

U.S. PATENT DOCUMENTS

| | | | |
|---|---|---|---|
| 5,451,505 A | 9/1995 | Dollinger | |
| 5,599,578 A | 2/1997 | Butland | |
| 5,845,264 A | 12/1998 | Nellhaus | |
| 5,974,150 A | 10/1999 | Kaish et al. | |
| 5,992,742 A * | 11/1999 | Sullivan et al. | 235/462.01 |
| 6,035,914 A | 3/2000 | Ramsey et al. | |
| 6,071,531 A | 6/2000 | Jona et al. | |
| 6,159,504 A | 12/2000 | Kumabe | |
| 6,214,766 B1 | 4/2001 | Kurrle | |
| 6,246,061 B1 | 6/2001 | Ramsey et al. | |
| 6,309,690 B1 | 10/2001 | Brogger et al. | |
| 6,402,986 B1 | 6/2002 | Jones, II et al. | |
| 6,458,595 B1 | 10/2002 | Selinfreund | |
| 6,522,945 B2 * | 2/2003 | Sleep et al. | 700/225 |
| 6,586,012 B2 | 7/2003 | Yu et al. | |
| 6,632,526 B1 | 10/2003 | Chandler et al. | |
| 6,647,649 B2 | 11/2003 | Hunt et al. | |
| 6,649,414 B1 | 11/2003 | Chandler et al. | |
| 6,696,091 B2 | 2/2004 | Thakur et al. | |
| 6,708,618 B1 | 3/2004 | Tsai | |
| 6,714,299 B2 | 3/2004 | Peterson et al. | |
| 6,773,812 B2 | 8/2004 | Chandler et al. | |
| 6,799,725 B1 * | 10/2004 | Hess et al. | 235/462.01 |
| 6,869,015 B2 * | 3/2005 | Cummings et al. | 235/462.25 |
| 6,892,178 B1 | 5/2005 | Zacharia | |
| 6,919,009 B2 | 7/2005 | Stonas et al. | |
| 6,948,068 B2 | 9/2005 | Lawandy et al. | |
| 6,968,231 B1 | 11/2005 | Silvian et al. | |
| 7,041,362 B2 | 5/2006 | Barbera-Guillem | |
| 7,052,737 B2 | 5/2006 | Kool et al. | |
| 7,089,420 B1 | 8/2006 | Durst et al. | |
| 7,094,305 B2 | 8/2006 | Cleary | |
| 7,129,506 B2 * | 10/2006 | Ross et al. | 250/556 |
| 7,162,035 B1 | 1/2007 | Durst et al. | |
| 7,207,490 B2 | 4/2007 | Schneider | |
| 7,256,398 B2 | 8/2007 | Ross et al. | |
| 7,378,675 B2 | 5/2008 | Ross et al. | |
| 7,392,950 B2 | 7/2008 | Walmsley et al. | |
| 7,394,997 B2 | 7/2008 | Mei et al. | |
| 7,507,588 B2 | 3/2009 | Mehrpouyan et al. | |
| 7,720,254 B2 | 5/2010 | Stierman et al. | |
| 7,752,137 B2 | 7/2010 | Dillon | |
| 7,773,749 B1 | 8/2010 | Durst et al. | |
| 7,831,042 B2 | 11/2010 | Stierman et al. | |
| 7,885,428 B2 | 2/2011 | Stierman et al. | |
| 7,995,196 B1 | 8/2011 | Fraser | |
| 2001/0037455 A1 | 11/2001 | Lawandy et al. | |
| 2002/0048822 A1 | 4/2002 | Rittenburg et al. | |
| 2002/0066543 A1 | 6/2002 | Lilly | |
| 2002/0129251 A1 | 9/2002 | Itakura et al. | |
| 2003/0064105 A1 | 4/2003 | Kim et al. | |
| 2003/0141375 A1 | 7/2003 | Lawandy | |
| 2004/0022355 A1 | 2/2004 | Kaiser et al. | |
| 2004/0061702 A1 | 4/2004 | Kincaid | |
| 2004/0126840 A1 | 7/2004 | Cheng et al. | |
| 2004/0166063 A1 | 8/2004 | Siegel | |
| 2004/0185481 A1 | 9/2004 | Numajiri | |
| 2005/0031838 A1 | 2/2005 | Lagunowich et al. | |
| 2005/0060171 A1 | 3/2005 | Molnar | |
| 2005/0100204 A1 | 5/2005 | Afzal et al. | |
| 2005/0108044 A1 | 5/2005 | Koster | |
| 2005/0112610 A1 | 5/2005 | Lee et al. | |
| 2006/0054506 A1 | 3/2006 | Natan et al. | |
| 2006/0119913 A1 | 6/2006 | Moon | |
| 2006/0131517 A1 | 6/2006 | Ross et al. | |
| 2007/0012783 A1 | 1/2007 | Mercolino | |
| 2007/0086625 A1 * | 4/2007 | Polli et al. | 382/115 |
| 2007/0172429 A1 | 7/2007 | Gao et al. | |
| 2008/0034426 A1 | 2/2008 | Stierman et al. | |
| 2009/0084859 A1 | 4/2009 | Lapstun et al. | |
| 2010/0128925 A1 | 5/2010 | Stierman et al. | |

FOREIGN PATENT DOCUMENTS

| | | | |
|---|---|---|---|
| EP | 0650546 B1 | 10/1997 | |
| EP | 1998710 | 12/2008 | |
| EP | 1999873 | 12/2008 | |
| EP | 2011008 | 1/2009 | |
| GB | 2220346 | * 10/1990 | |
| JP | 6-298650 A | 10/1994 | |
| WO | 99/17486 A1 | 4/1999 | |
| WO | 0151915 A1 | 7/2001 | |
| WO | 03039648 A2 | 5/2003 | |
| WO | 2004/041328 A2 | 5/2004 | |
| WO | 2004038645 A1 | 5/2004 | |
| WO | 2004/063752 A1 | 7/2004 | |
| WO | 2005/111127 A1 | 11/2005 | |
| WO | 2007002009 A2 | 1/2007 | |
| WO | 2007002016 A2 | 1/2007 | |
| WO | 2007021971 A2 | 2/2007 | |
| WO | 2007106512 A2 | 9/2007 | |
| WO | 2007106514 A3 | 9/2007 | |
| WO | 2007106515 A3 | 9/2007 | |
| WO | 2007149127 A1 | 12/2007 | |

OTHER PUBLICATIONS

Golub, T.R., et al., Molecular Classification of Cancer: Class Discovery and Class Prediction by Gene Expression Monitoring, Science, Oct. 15, 1999, pp. 531-537, vol. 286, www.sciencemag.org.

Zhi, Z., et al., Multianalyte immunoassay with self-assembled addressable microparticle array on a chip, Analytical Biochemistry, 2003, pp. 236-243, vol. 318, Elsevier Science.

Wolfrum, C., et al., Oligonucleotides as Coding Molecules in an Anti-Counterfeiting System, Nucleosides, Nucleotides, and Nucleic Acids, 2005, pp. 1069-1074, vol. 24 (5-7).

Co-pending U.S. Appl. No. 11/455,817 dated Jun. 20, 2006.

Patent Cooperation Treaty, International Preliminary Report on Patentability, Dec. 22, 2008, PCT/US2006/062374.

Patent Cooperation Treaty, Written Opinion of the International Search Authority, Jul. 31, 2007, PCT/US2006/062374.

Patent Cooperation Treaty, International Preliminary Report on Patentability, Mar. 17, 2009, PCT/US2006/023876.

Patent Cooperation Treaty, Written Opinion of the International Search Authority, Apr. 16, 2008, PCT/US2006/023876.

Patent Cooperation Treaty, International Preliminary Report on Patentability, Dec. 24, 2007, PCT/US2006/023868.

Patent Cooperation Treaty, Written Opinion of the International Search Authority, Apr. 25, 2007, PCT/US2006/023868.

European Patent Office, Supplementary European Search Report for European Patent application No. 06785135.2-2210 dated Mar. 2, 2012.

Barker, Robert L., et al., "Cytometric Detection of DNA Amplified with Fluorescent Primers: Application to Analysis of Clonal bcl-2 and IgH Gene Rearrangements in Malignant Lymphomas", Blood, 83(4):1079-1085 (Feb. 15, 1994).

Euliss, Larken E., et al., "Imparting size, shape and composition control of materials for nanomedicine", Chem. Soc. Rev. 35:1095-1104 (2006).

Finkel, Nancy H., et al., "The Barcoding Microworld", Analytical Chemistry, 353A-359A (Oct. 1, 2004).

Flurer, Cheryl L., et al., "Chemical profiling of pharmaceuticals by capillary electrophoresis in the determination of drug origin", Journal of Chromatography A 674:153-163 (1994).

Fulton, R. Jerrold, et al., "Advanced multiplexed analysis with the FlowMetrix system", Clinical Chemistry, 43 (9):1749-1756 (1997).

Fulwyler, Mack J., et al., "Flow Microsphere Immunoassay for the Quantitative and Simultaneous Detection of Multiple Soluble Analytes", Methods in Cell Biology 33: 613-629 (1990).

Green, Michael D., et al., "Short communication: Authentication of artemether, artesunate and dihydroartemisinin antimalarial tablets using a simple colorimetric method", Tropical Medicine and International Health, 6(12):980-982 (Dec. 2001).

Ham, Martijin Ten, "Health Risks of Counterfeit Pharmaceuticals", Drug Safety, 26(14):991-997 (2003).

McHugh, Thomas M., "Flow Microsphere Immunoassay for the Quantitative and Simultaneous Detection of Multiple Soluble Analytes", Methods in Cell Biology, 42:575-595 (1994).

Olsen, Bernard A., et al., "Screening for Counterfeit Drugs Using Near-Infrared Spectroscopy", Pharmaceutical Technology, 62, 64, 66, 68, 70-71 and 95 (Jun. 2002).

Pachaly, Von P., et al., "Einfache dunnschichtchromatographische Identitatsprufung von Wirkstoffen in Fertigarzneimitteln" Pharm. Ind. 55(3):259-267 (1993).

Rolland, Jason P., et al., "High-Resolution Soft Lithography: Enabling Materials for Nanotechnologies", Angew. Chem. 116:5920-5923 (2004).

Rolland, Jason P., et al., "Direct Fabrication and Harvesting of Monodisperse, Shape-Specific Nanobiomaterials", J. Am. Chem. Soc. (Mar. 28, 2005).

Scafi, Sergio Henrique Frasson, "Identification of counterfeit drugs using near-infrared spectroscopy", Analyst, 126:2218-224 (Nov. 19, 2001).

Yang, G., et al., "Detection of hepatitis B virus in plasma using flow cytometric analyses of polymerase chain reaction-amplified DNA incorporating digooxigenin-11-dUTP", Blood, 81:1083-1088 (1993).

Han, Mingyong, et al. "Quantum-dot-tagged microbeads for multiplexed optical coding of biomolecules," Nature Biotechnology, 19:631-635 (2001).

* cited by examiner

METHODS FOR QUALITY CONTROL

CROSS-REFERENCES TO RELATED APPLICATIONS

This application is a Continuation-in-Part of U.S. patent application Ser. No. 11/455,817 filed Jun. 20, 2006, which claims priority to U.S. Provisional Patent Application No. 60/692,225 filed Jun. 20, 2005.

FIELD OF THE INVENTION

The present invention relates to methods for quality control of surface coating in a manufacturing process. In particular, the invention provides a method to detect density, efficiency and/or uniformity of coating applied to the surface of a manufactured article. The invention further relates to incorporation of a unique product signature for authenticating, tracking or tracing articles manufactured according to the quality control procedures of the invention. The invention further relates to providing a means to detect proper and/or improper handling or storage of articles manufactured according to the quality control procedure of the invention. The present invention also relates to a method for assuring that product contents' match product's label and extends the utility of using the count or relative count of microparticles or symbols to create an authentication code in order to minimize the occurrence of packaging mismatch errors.

BACKGROUND OF THE INVENTION

In surface coating processes, the density, efficiency and/or uniformity of the coating(s) are parameters that typically affect performance of products such as stents, hemostatic sponges or other medical devices. Typically, biologics or drugs are incorporated in such coatings, and measuring the density, uniformity, or coating efficiency associated with these compounds is often difficult or impossible without destruction of at least a portion of the coating.

Further, manufacturing processes often involve exposure of articles to critical environmental conditions, such as temperature, humidity, or electromagnetic radiation. It is not always easy to assure that every article from a manufacturing line has been properly exposed to critical environmental conditions, or that every article has not been exposed to unacceptable environmental conditions. Sometimes, only portions of the article are inadequately or unacceptably exposed. Similarly, handling of products after release often requires that they are not exposed to unacceptable environmental conditions.

Additionally, manufacturing processes often involve quality control processes to assure that product contents match the product's label. Failure of such control processes may result in occurrence of packaging mismatch, with potential adverse consequences to the product's end user.

Products that can benefit from quality control of the density, efficiency and/or uniformity of the coating include single-use surgical devices, implantables, sutures, products sterilized according to custom procedure by customers after purchase, hysteroscope, drug coated contact lenses, reagent coatings for diagnostic products, and enteric coatings on pharmaceuticals.

Products that can benefit from monitoring required environmental exposure or exposure to unacceptable environmental conditions include products stored and distributed in cold-chain systems, sunscreens, and consumer products with finite shelf life.

Products that can benefit quality control processes to assure that product contents match the product's label include consumer products, pharmaceutical products, medical diagnostics, and medical devices.

Further, counterfeiting of manufactured goods, including those that incorporate coated surfaces is a global issue. It is estimated that 5% of all world trade in branded goods is counterfeit (ten Ham, *Drug Saf.*, 2003, 26: 991-7). A counterfeit product often appears confusingly similar to that of a genuine product. The material of a counterfeit product may be the same as, or different from the material of a genuine product. Often the counterfeiting product has inferior quality as compared to that of a genuine product. There is a continuing need to develop novel methods to combat counterfeiting at the manufacturing stage and for detection counterfeit goods in the distribution chain.

Methods have been developed to identify genuine products and distinguish them from counterfeit products. For example, various analytical methods have been used to detect components in pharmaceutical products, with emphasis on the identification of differences among manufacturers that can be used for source verification in suspect/counterfeit cases. Such methods include, but are not limited to, capillary electrophoresis (Flurer et al, *Journal of Chromatography, A,* 1994, 674: 153-63), thin-layer chromatography (Pachaly et al., *Pharmazeutische Industrie,* 1993, 55: 259-67), near-infrared spectroscopy (Scafi et al, *Analyst.* 2001, 126: 2218-24; and Olsen et al., *Pharmaceutical Technology North America,* 2002, 26: 62-71), and calorimetric assay (Green et al, *Tropical Medicine & International Health,* 2001, 6: 980-982).

Other methods have been developed to establish identity and source of the product, sometimes including a pharmaceutical product, by marking the product. For example, bar code symbols placed on the outside of the medication may be used for prescription medication identification (U.S. Pat. No. 5,845,264); a mixture of at least two photochromic compounds that have different absorption maxima in the activated state may be incorporated into a carrier composition, e.g., ink, paint, fiber or polymer to form the authenticating display data on the article (U.S. Pat. No. 5,289,547); a solution of a target nucleic acid may be incorporated in an object for security crypto-marking of the object (U.S. Pat. No. 5,139,812); a hapten may be associated with the product as a marker (U.S. Pat. No. 5,429,952); compositions that are uniquely luminescent may be incorporated or applied to materials for verifying products or documents (U.S. Pat. No. 6,402,986); and constituents intrinsically located or extrinsically placed in an object (such as a pharmaceutical) may be detected by x-ray fluorescence analysis to identify or verify the object or its point of manufacture (US 20040022355). In addition, U.S. Pat. No. 5,599,578 describes a method for labeling an object for its verification by applying a mark to said object with a visible ink that contains a component that is invisible to the naked eye, such as a dye that is visible only in the presence of selected radiation, or an ink that displays a selected measurable electrical resistivity, or an ink containing a biologic marker. WO 2004041328 describes methods for marking a pharmaceutical product, container or pharmaceutical packaging system with a scent to establish the identity and/or source of the pharmaceutical.

The substance(s) used to mark a product can be visible, such as a dye or colored molecule. They can also be invisible to the unaided eyes, thus are a "covert" marker of a substance. Covert markers are typically more difficult to replicate, simulate, alter, transpose, and are less subject to tampering. WO 2005111127 describes a method for incorporating covert markers into an article in the form of metals and their salts and oxides into plastics, then detecting net changes in magnetic field around said article.

Microparticles have been used to mark a product for authentication. In some embodiments, microparticles have been used as the "cargo" to host the coding elements like molecules or nanoparticles with identifiable features (Finkel et al., Oct. 1, 2004, *Analytical Chemistry*, 352A-359A, and references therein). U.S. Pat. No. 4,053,433 describes a method of marking a substance with microparticles that are encoded with an orderly sequence of visually distinguishable colored segments that can be decoded with a microscope or other magnifying device. Additionally, microparticles have been used as part of the coding element, where the physical properties of the microparticles are used as the coding elements, and most code deciphering is accomplished by recognizing a physical pattern formed by the compilation of various microparticles (Finkel et al., 2004 supra and references therein). U.S. Pat. No. 4,767,205 discloses an identification method involving an identification code that is based upon a selected number of groups of microparticles, wherein each group is made of highly uniform microparticles of substantially the same uniform size, shape and color with the specific combination of size, shape and color in one group not being repeated in any other group. U.S. Pat. No. 6,647,649 discloses a process for marking an article by applying thereto a tag, which comprises a plurality of microparticles having two or more distinguishable marker layers corresponding to a predetermined numeric code.

Despite these efforts, drug and medical devices counterfeiting remains a worldwide problem. There is a continuing need to develop novel methods to combat counterfeit drugs and devices at the manufacturing stage and for detection in the distribution chain. One effective way to fight counterfeiting is to mark a product with an authentication or product identification code that is not easily imitated or counterfeited. The present invention provides a methodology for quality control of surface coatings that is also readily adaptable to product authentication by incorporating a unique product signature for authenticating, tracking or tracing articles manufactured according to the quality control procedures of the invention. The invention further relates to providing a means to detect proper and/or improper handling or storage of articles manufactured according to the quality control procedure of the invention.

The present invention also relates to a method for assuring that product contents' match product's label using microparticulate taggants having different detectable physical properties, wherein each combination of properties is used as an encoding bit to create codes. The present invention thus further extends the utility of using the count or relative count of microparticles or symbols to create an authentication code in order to minimize the occurrence of packaging mismatch errors by providing a coding system that can be incorporated into product contents, into or onto product packaging containers, and into or onto product labels. The coding system provides for multiple checkpoints to assure against mix-up errors.

SUMMARY OF THE INVENTION

Density, efficiency and/or uniformity of a coating are often important for product performance, and otherwise difficult to assess without complex and expensive instrumentation, often in conjunction with a destructive testing method. It is one object of the present invention to provide a method for quality control of surface coating in a manufacturing process, including the processes of spraying, brushing, dipping, and immersion, by a method that does not require destructive testing of the article.

It is another object of the invention to provide a method for simple, low cost and easy to implement quality control measure to assure that articles in a manufacturing process are within tolerances for environment exposure.

It is yet another object of the invention to provide a quality control measure that allow in-line, every-piece, real-time monitoring, real time adjustment of manufacturing parameters and further ensures easy identification of affected product for quarantine and/or disposal.

It is also another object of the invention to couple the quality control methodology of the present invention to a unique, hard to imitate product signature or product identification code useful to authenticate, track or trace manufactured articles. Methods of the invention are easy to implement and can be covert, and difficult to replicate, simulate, alter, or transpose, and resist tampering and inadvertent or intentional alteration.

It is also another object of the invention to provide a means to detect proper and/or improper handling or storage of the article (as may affect stability and product performance), whether in the manufacturing process or after supply and distribution of the article. In this object, a tracer which may be one or more elements of a product authentication code used to assure manufacturing processes undergoes a detectable change after exposure to environmental factors, such as high or low temperature thresholds, humidity, or radiation exposure.

These and other objectives are attained generally by associating a population of easy-to-measure entities with coating medium of the manufactured article, such that the counts or relative counts of entities correlate with deposition of at least one coating medium on the article. Preferably, in a manufacturing process wherein more than one component is coated on the article's surface, coating of each component is correlated with a different cluster of entities. Preferably, the entities are inert, non-toxic, and bioabsorbable.

In one embodiment of the invention, a coated article is provided with a product authentication code wherein the product authentication code is encoded by a signature array of a population of entities associated with the product, wherein the signature array comprises information about the counts or relative counts of entities of at least two distinct clusters of entities within the population, wherein the counts or relative counts of entities within at least one of said clusters correlates with the deposition of a coating on the article.

In yet another embodiment of the invention, a coated article is provided with a product authentication code wherein the product authentication code is encoded by a signature array of a population of entities associated with the product, wherein the signature array comprises information about the counts or relative counts of entities of at least two distinct clusters of entities within the population, wherein the counts or relative counts of entities within at least one of said clusters changes in response to exposure of the product to an environmental stimulus, such as maximum acceptable temperature, minimum acceptable temperature, maximum acceptable humidity, minimum acceptable humidity, or maximum acceptable level of electromagnetic radiation.

One aspect of the invention comprises the steps of: a) associating a population of entities with a product during the manufacturing process, wherein the counts or relative counts of entities correlates with the deposition of at least one coating component on the article; b) analyzing the product to obtain a measured value of the counts, relative counts, and/or uniformity of deposition of a least one such population of entities; c) comparing the measured counts, relative counts, and/or uniformity of deposition of entities with a corresponding expected counts, relative count, and/or uniformity of deposition acceptance value; and d) releasing products manufactured by the manufacturing process when the measured value is within and acceptance range of the expected value.

Another aspect of the invention comprises the steps of: a) associating a population of entities with a product during the manufacturing process, wherein the population of entities comprises at least two distinct clusters of entities having detectable counts or relative counts of entities per cluster and wherein the counts or relative counts of entities within at least one of said clusters changes in response to exposure of the product to an environmental stimulus such as a maximum acceptable temperature, a minimum acceptable temperature, a maximum acceptable humidity, a minimum acceptable humidity, or a maximum acceptable level of electromagnetic radiation; b) analyzing the product to obtain a measured value of the counts of said cluster(s) that change(s) in response of exposure of the product to an environmental stimulus; c) comparing the measured counts with a corresponding expected counts acceptance value; and d) releasing products manufactured by the manufacturing process when the measured value is within an acceptable range of the expected value.

Another general aspect of the invention is an improvement to a product, wherein the improvement is a product authentication code that is coupled to a quality control methodology of the present invention.

One other general aspect of the present invention is a method of authenticating a product, comprising the steps of: a) associating a population of entities with the product, wherein the population comprises at least two distinct clusters of entities having detectable counts or relative counts of entities per cluster; b) assigning a signature array of the population of entities to the product as a product authentication code, wherein the signature array comprises information about the counts or relative counts of entities of at least two distinct clusters of entities within the population; wherein information about the signature array and the product authentication code is recorded; c) analyzing the product to obtain a measured signature array of the population of entities associated with the product; d) comparing the measured signature array with that which is expected based on the recorded information; and e) accepting the product as authenticate when the measured signature array matches that which is expected.

Another general aspect of the invention is a method for quality control and release of products from a manufacturing process, comprising the steps of: a) associating a population of entities with a product during the manufacturing process, wherein the population of entities comprises at least two distinct clusters of entities having detectable counts or relative counts of entities per cluster, wherein a signature array that comprises information about the counts or relative counts of entities of the at least two distinct clusters of entities is recorded; b) analyzing the product to obtain a measured signature array of the population of entities associated with the product; c) comparing the measured signature array with that which is expected based on the recorded information; and d) releasing products manufactured by the manufacturing process when the measured signature array matches that which is expected.

In a particular embodiment of the invention, the population of entities comprises a combination or plurality of microparticles. In a preferred embodiment of this invention, the coating to be deposited is a biologic and the manufactured article is a medical device or product.

DETAILED DESCRIPTION OF PREFERRED EMBODIMENTS

Figure 1:
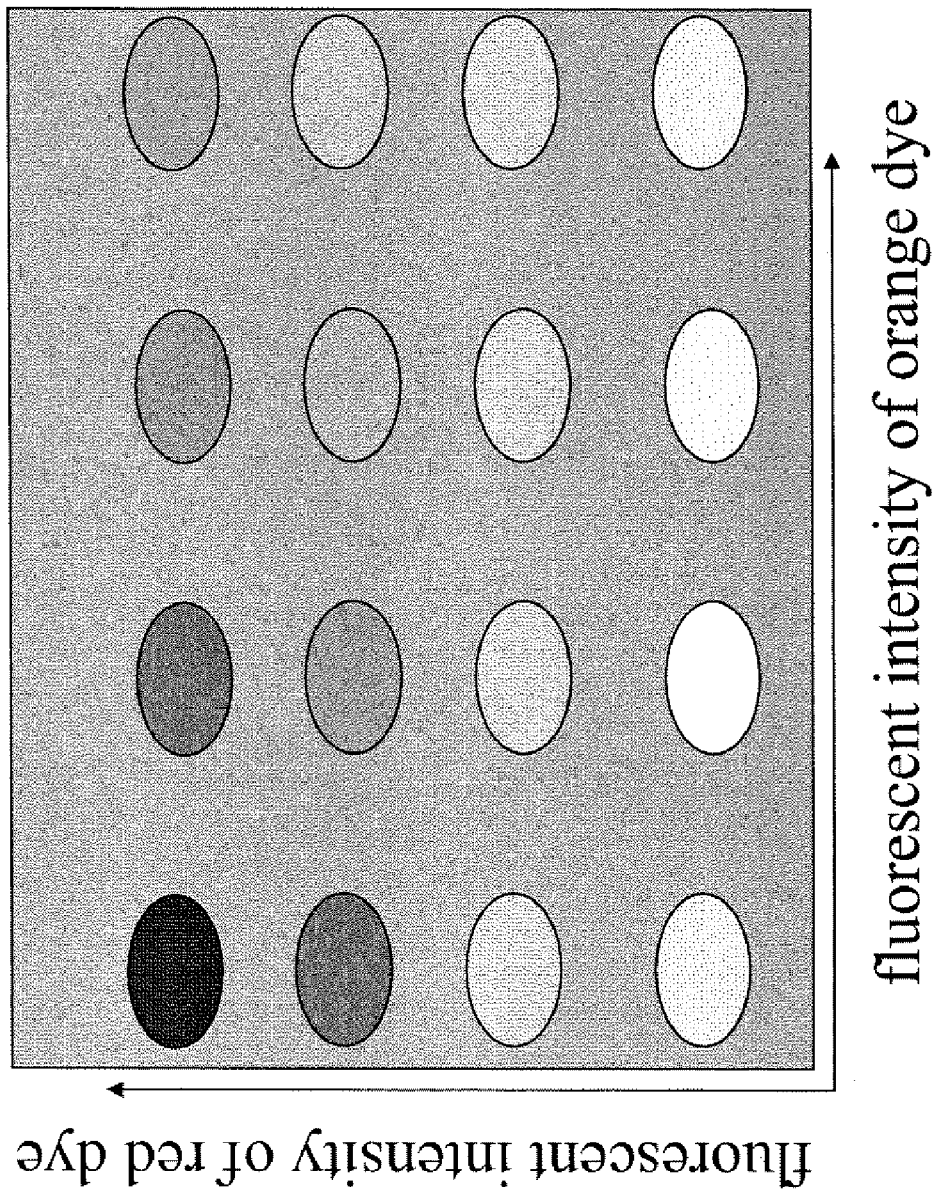
FIG. 1 illustrates the classification into clusters of a population of heterogeneous microparticles labeled with different intensities of two fluorescent dyes, red and orange. X-axis represents fluorescent intensity of orange dye and Y-axis represents fluorescent intensity of the red dye.

All publications cited below are hereby incorporated by reference. Unless defined otherwise, all technical and scientific terms used herein will have the commonly understood meaning to one of ordinary skill in the art to which this invention pertains.

It must be noted that as used herein and in the appended claims, the singular forms "a," "an," and "the" include plural reference unless the context clearly dictates otherwise. Thus, for example, a reference to "a population of entities" is a reference to one or more populations of entities and includes equivalents thereof known to those skilled in the art and so forth.

As used herein, the term "array" means a collection of data items arranged in such a way so that each data item in the array can be located.

As used herein, a "cluster of entities" or a "cluster" means a classification of at least two entities that are grouped together because they share one or more discretely measurable common properties. In particular embodiments of the invention, the entities within "a cluster of entities" share one, two, three, four, five, six, seven, eight, nine, ten, or more discretely measurable common properties.

As used herein, the "count of entities per cluster", the "number of entities per cluster", the "count (or number) of entities within a cluster", and the "count (or number) of entities of a cluster" are used interchangeably to mean the number or sum total of entities within a cluster. The "count of entities per cluster" can be obtained by counting discrete entities within the cluster by means such as an automated counter or manual counting method.

As used herein, the term "pharmaceutical product" includes drugs, pharmaceutical formulations and medical devices.

As used herein, the term "counterfeit" when applied as a description to a product or drug means a product made in imitation of a genuine product or drug with intent to deceive. As used herein, the terms "counterfeit drug" and "counterfeit pharmaceutical product" may be used interchangeably. For example, a counterfeit drug is a composition that has not received approval by a governmental authority (e.g., the Food and Drug Administration of the United States) to be safe and efficacious for medical purpose in human subjects, but is labeled as a genuine pharmaceutical product.

Another example of a counterfeit drug is a pharmaceutical composition that has been tampered, such as by dilution. A "counterfeit drug" also includes a composition that contains the same active ingredient(s) as that of a genuine pharmaceutical product, but is made by a party who is not legally entitled to do so, and that party passes off the composition as that of a genuine pharmaceutical product. A "counterfeit drug" as used herein also includes drug diversion or "grey market drug". Drug diversion occurs when a counterfeiter acquires genuine, non-counterfeit drugs that are targeted for one market and sells them in a different market for a profit. The counterfeiter does this to circumvent the manufacturer's goal of controlling the supply of the drugs in a particular market. As a consequence, the counterfeiter benefits from the sales in that limited supply market or in the diverted sales market.

As used herein, the term "data item" or "datum" means a single member of data.

As used herein, the term "data" means two or more individual facts or pieces of information.

As used herein, a "discretely measurable common property" is a property of or associated with each individual entity within a single cluster, and said property can be measured from the individual entity. The discretely measurable common property allows an entity to be assigned into a particular cluster. Entities having the same set of one or more discretely measurable common properties can be assigned into the same cluster. Entities having different sets of discretely measurable common properties can be assigned into distinct clusters.

Examples of "discretely measurable common property" include, but are not limited to, the properties of one or more tags associated with entities of a cluster, such as the fluorescent intensity or spectra when the entity is labeled with a fluorescent tag, the sizes of the entities, the shape of the entities, and other properties of the entities, such as being magnetic or not, density, or solid characterization, or the nucleotide sequence or amino acid sequence when the entities are composed of nucleic acid molecules or peptides/polypeptides.

As used herein, "distinct clusters of entities" means clusters that are different because entities within one cluster having at least one discretely measurable common property that is not shared with the entities within the other cluster(s). Thus clusters of entities can be distinguished from one and another by the measurement of any of the discretely measurable common properties shared by entities within one cluster but not by entities within the other cluster(s)—the distinct discretely measurable common properties.

For example, the clusters of entities can be distinguished by sizes, density or solidity including elasticity, brittle fracture, water-content etc. The particle size can be measured, for example, in a flow cytometry apparatus by so-called forward or small-angle scatter light or by microscopic examination.

The clusters of entities can also be distinguished by shape. The shape of the particle can be discriminated, for example, by flow cytometry, by high-resolution slit-scanning method or by microscopic examination. The shape of a printed dot, for example, can be measured by a scanner. The clusters of entities can further be distinguished by tags, such as by fluorescent dyes with different emission wavelengths. Even when they are labeled with the same tag(s), the clusters of entities can still be distinguished because of different concentrations, intensity, or amounts of the tag associated with the entities, or the different ratios of tags on individual entities. Clusters of entities can be distinguished even when all entities share one or more discretely measurable common properties (e.g., particle size and particle shape), but do not share at least one other discretely measurable common property (e.g., intensity or amount of fluorescent tag per entity).

Methods known to a person skilled in the art can be used to measure the quality or quantity of tags. In addition, the clusters of entities can be differentiated by other property or characteristic of the entities, such as being magnetic or not. When the entities are composed of or labeled with nucleic acid or peptide molecules, the clusters of entities can be differentiated by their sequences.

It is understood by a person skilled in the art that there is a basic distinction between measurement and counting. The result of counting, for example, the count of entities within a cluster, is exact because it involves discrete entities that are not subdivided into fractions. The result of measurement, on the other hand, involves measurement units that may be subdivided into smaller and smaller fractions and is thus always an estimate. A good measurement should be both accurate and precise. Accuracy is determined by the care taken by the person making the measurement and the condition of the instrument; a worn or broken instrument or one carelessly used may give an inaccurate result. Precision, on the other hand, is determined by the design of the instrument; the finer the graduations on the instrument's scale and the greater the ease with which they can be read, the more precise the measurement. The choice of the instrument used should be appropriate to the desired precision of the results. A person skilled in the art knows how to choose an appropriate instrument for a particular measurement.

In order to detect the count or relative count of entities within distinct clusters of a population, the clusters of entities must first be distinguished based on the measurement of the distinct discretely measurable common property or properties. It is readily apparent to a skilled artisan that the detection of the count or relative count of entities within distinct clusters of a population thus depends on the accuracy and precision of the measurement of the distinct discretely measurable common property or properties.

If the distinct discretely measurable common property can not be reproducibly measured, the clusters can not be distinguished with confidence, thus the count or relative count of entities within distinct clusters can not be detected. Therefore, a condition precedent to detecting count or relative count of entities within distinct clusters of a population is the reproducible measurement of the distinct discretely measurable common property. In the present invention, at least two distinct clusters of entities are mixed in a population wherein the clusters are distinguishable by one or more distinct discretely measurable common properties that can be reproducibly measured. Thus, the counts or relative counts of entities within the distinct clusters of the population of the present invention are detectable.

As used herein, the terms "drug" and "pharmaceutical product" may be used interchangeably. The terms mean a composition that has received approval by a governmental authority (e.g., the Food and Drug Administration of the United States) to be safe and efficacious for medical purpose in human subjects. The "drug" can be in any physical state, such as being solid, liquid, or semi-liquid. The "drug" can be in any form of formulation, such as being an oral, topical, injectable, or parental pharmaceutical product.

As used herein, the term "entity" means a thing or composition that can exist separately or independently from other things. Examples of entities that can be used in the present invention include, but are not limited to, microparticles, printed symbols, nucleic acid molecules, or peptides/polypeptides.

As used herein, the terms "microparticle", "microsphere", "microbead", "bead", "microsphere", and "particle" are used interchangeably and bear equivalent meanings with respect to their particulate nature, understanding that particles can have various shapes and sizes. Preferred particles range in size from approximately 10 nm to about 200 µm in diameter or width and height in the case of nonspherical particles. For example, the particles can have a size of 0.05-50 µm, 0.1-20 µm, 1-20 µm, or 3-10 µm in diameter. The microparticles can have a different shape, such as a sphere, cube, rod or pyramid.

Those of ordinary skill in the art can use microspheres of various compositions. For example, styrene monomers polymerized into hard rigid latex spheres have been used as calibration aids at high magnifications. These latex spheres are known for their high level of inertness in the electron beam, and clusters constructed from groups of such particles within non-overlapping size ranges of approximately 0.05 to 2 microns may be detected by electron microscopy or light-scattering investigations. Likewise, the particles can be made of many other types of materials. For example, the microparticles can be made of polystyrene or latex material. Other types of acceptable polymeric microspheres include, but are not limited to, brominated polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, POLYOX, EUDRAGIT, sugar spheres, hydrofuran, PLGA (poly(lactic coglycolic acid)) or combinations thereof. In general, such particles can be made by a copolymerization process wherein monomers, e.g., unsaturated aldehydes or acrylates, are allowed to polymerize in the presence of one or more tags, e.g., fluorescein isothiocynate (FITC), in the reaction mixture (see for example U.S. Pat. No. 4,267,234 issued to Rembaum; U.S. Pat. No. 4,267,235 Rembaum et al; U.S. Pat. No. 4,552,812, Margel et al.; U.S. Pat. No. 4,677,138, Margel). The microparticles can be produced, for example, by extrusion or spherenization.

In another embodiment, the entities can be printed symbols. As used herein, the term "printed symbol" means any symbol that is placed on or otherwise applied to a surface of a material. The "printed symbol" can be in any form or shape. For example, it can be dots, letters, or other visible or invisible signs. The "printed symbol" can have different shapes, such as square, circle, triangle, diamond, or any other shapes that can be distinctively measured. The "printed symbol" can also have different fonts or sizes. For example, the printed symbols can have a size of 0.05-1 µm, 1-20 µm, 50-100 µm, or 0.1-5 mm in diameter, width, or length in the cases where the printed symbols are not round in shape. The "printed symbol" can be any printable characters selected among many alternative identities, for example, symbols or Greek alphabet characters, the Roman alphabet characters, or any other letters of any language. Further, the font size and or style of the "printed symbol" could be replaced with any number of alternatives, for example, font color, italics, striking-through, highlighting or the like. Whole words or logos may replace individual characters to be used as "printed symbols". The "printed symbol" can also be any symbols, including those designated as symbols in the word-processing program MICROSOFT WORD.

The "printed symbol" can be placed on or applied to the surface of a material by a variety of means. For example, it can be applied to a printable surface by printing; or it can be applied to a surface by dropping, spraying, painting, rolling coating, embossing, debossing, etc.

Additionally, microprinting is an alternative to the conventional printing used in this example. Microprinting is an anti-counterfeiting technique used most often on currency and bank checks, as well as various other items of value. Microprinting involves printing very small text, usually too small to read with the naked eye, onto the note or item. Microprint is frequently hidden in an inconspicuous, unnoticeable area on the note or item, but may be placed in a prominent location on the item, and may even be labeled with an "MP" symbol as a warning that the note or item contains microprinting. For example, U.S. Pat. No. 6,214,766 relates generally to a method for producing security paper which involves printing microdot images using a colorless ink containing starch, such dots to be revealed by exposure to iodine.

To increase the per volume information content, the entity can be labeled with one or more tags that are visible or invisible to naked eyes. The term "tag" or "taggant" as used herein can be any composition that is suitable for the purpose of detecting or identification. The tag can be overt, covert, or invisible or otherwise difficult to detect on individual entities or small numbers of entities, yet having an overt signal detectable from all or a larger number of entities. For example, the entity can be labeled with one or more colors, fluorescent dyes, ultraviolet radiation dyes, luminescent compositions, hapten, nucleotides, polypeptides, or scents. A single entity can be labeled with more than one tag of the same or different types. For example, a particle can be labeled with two or more discretely distinguishable dyes in varying proportion; or a particle can be labeled with a nucleotide and a fluorescent dye. Any of the known tags and the combinations of the tags with entities can be used in the invention. Methods known to those skilled in the art can be used to label an entity with one or more tag. For example, U.S. Pat. No. 6,632,526 teaches methods of dyeing or staining microspheres with at least two fluorescent dyes in such a manner that intra-sample variation of dye concentrations are substantially minimized. The entity can be a segmented particle whose composition is varied along the diameter or the length of the particle. U.S. Pat. No. 6,919,009 teaches methods of manufacture of rod-shaped particles.

In one particular embodiment, the entity can be an entity that is labeled with or affixed to other entities. For example, the entity can be a symbol printed with an ink containing microparticles. Another example of an entity, according to this embodiment, is a particle that is covalently or non-covalently affixed with one or more other particles. US 20060054506 describes submicron-sized particles or labels that can be covalently or non-covalently affixed to entities of interest for the purpose of quantification, location, identification, tracking, and diagnosis.

The entity that can be used in the present invention preferably can be ingestible and/or non-toxic in amounts used. For example, the entity can be a liposome microparticle, i.e., a particle formed by a lipid bilayer enclosing an aqueous compartment. The entity can also be a microparticle made of pulverized cellulose material, see for example the abstract of JP0 6,298,650. The entity can further be microparticles made of calcium, such as milk calcium, inorganic calcium or organic calcium. For example, edible oil-containing calcium microparticles can be obtained following the teaching of U.S. Pat. No. 6,159,504. Biodegradable polymers, such as dextran and polylactic acid, can also be used to prepare ingestible microparticles. In addition, the edible microparticles include solid lipophilic microparticles comprising a lipophilic substance, hyaluronic acid or an inorganic salt thereof. Exemplary lipophilic particles are disclosed in US 20030064105.

The entity can be magnetic. U.S. Pat. No. 6,773,812 describes hybrid microspheres constructed using fluorescent or luminescent microspheres and magnetic nanoparticles. Distinct clusters of microspheres can be constructed based on fluorescent intensities by analogy to the clusters described in Example 1 infra, and separations can be affected based on the variable degree of magnetic content to aid in the analysis of the cluster membership on devices like the Immunicon CELLSEARCH instrument. The various microspheres disclosed in U.S. Pat. No. 6,773,812 can be used in the present invention. The particles can also have any other property that facilitates collection, separation, or identification of the particles.

The entity can also be made of chemically inert materials to enhance the survival of the entity in a chemical or biological environment, including materials resistant to heat, high or low pH, etc. The entity can further be made of materials that are non-toxic, or materials that can serve as carriers for the active ingredient. The entity can even be made from the active ingredient of a pharmaceutical product.

As used herein, a "population of entities" or a "population" means a collection of a combination or plurality of entities that include two or more distinct clusters of entities, wherein entities within one cluster have one or more discretely measurable common properties that are different from that of entities within another cluster from the same population.

As used herein, the term "relative counts of entities per cluster" means a ratio of the count of entities per cluster relative to another number. In some embodiments, the other number is the count of entities within a different cluster. In other embodiments, the other number is the total count of entities within two or more clusters of a population of entities. In other embodiments, the other number is representative of the amount or concentration of the cluster or the population of entities, such as unit volume or weight of the cluster or the population of entities. In yet other embodiments, the other number is representative of the amount or concentration of a product the cluster is associated with, or the amount or concentration of a portion or a component of the product.

As used herein, the term "a representative number of entities within a population of entities" refers to a fraction or a portion of the population of entities which contains the same clusters of entities and the same count of entities per unit of each cluster as those of the population.

For illustrative purpose, in one specific embodiment of the invention, the population of entities is composed of microparticles each simultaneously labeled with two or more fluorescent dyes, for example, according to U.S. Pat. No. 6,632,526 or U.S. Pat. No. 6,649,414. The microparticles can also be purchased from a commercial source, such as Luminex Corporation (Austin, Tex.). For example, the particles can be labeled with two dyes, such as a red fluorescent dye, 1,3-bis [(1,3-dihydro-1,3,3-trimethyl-2H-indol-2-ylidene)methyl]-2,4-dihydroxy-cyclobutenediylium, bis(inner salt) (Dye 1) and an orange fluorescent dye, 2-(3,5-dimethylpyrrol-2-yl)-4-(3,5-dimethyl-2H-pyrrol-2-ylidene)-3-hydroxy-2-cyclobuten-1-one (Dye 2). As is readily appreciated, other combinations of dyes with other colors and other chemical compositions can also be used to label microparticles. One skilled in the art can select among a variety of suitable dyes such as, for example, the dyes recited in U.S. Pat. No. 6,649,414, depending upon desired emission/absorption and hydrophobic properties, etc. Where fluorescent dyes are used, the dyes are chosen such that the emission maxima of the dyes used preferably falls about in the center of the fluorescence detection channels of the measurement device used. Preferably the dyes used have emission maxima separated by greater than 10 nm, 25 nm, or 50 nm from each other.

Microparticles within the population are heterogeneous because they do not share at least one distinctly measurable property (e.g., intensity or amount of fluorescent tag per entity). The fluorescent intensity of the red or orange dye on each microparticle can be measured by flow cytometry. In one example, the measurement device is a Becton Dickinson FACScan flow cytometer. The microparticles within the population can be classified into clusters based on the intensities of the red and orange dyes on individual microparticles. As shown in FIG. 1, each filled oval dot represents a cluster of microparticles that are commonly labeled with the specified intensities of red and orange dyes. Microparticles within one cluster are distinct from those within each other cluster because they are labeled with different intensities of the red dye, the orange dye, or both the red and orange dyes.

Figure 2:
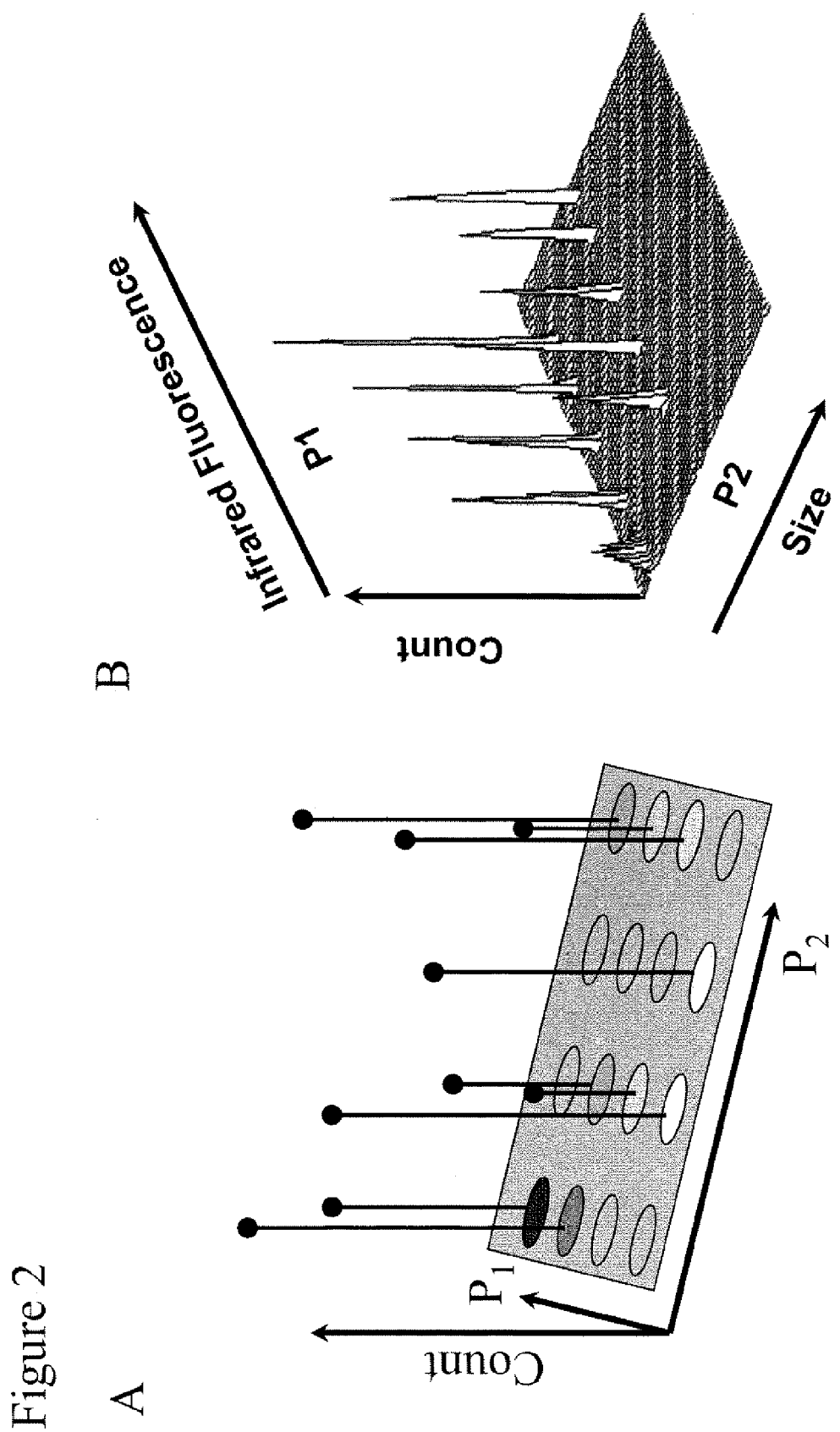
FIG. 2A illustrates how a signature array of a population of heterogeneous microparticles is constructed from the clusters of FIG. 1. Note that the signature array includes the counts or relative counts of entities within each of the at least two distinct clusters of entities.
FIG. 2B illustrates a signature array of a population of microparticles comprising ten (10) distinct clusters of microparticles classified into clusters by two discretely measurable common properties (i.e. their apparent size and relative infrared fluorescent intensity).

As used herein, "a signature array of a population of entities" is an array comprising information about the counts or relative counts of entities of at least two distinct clusters of entities within the population. Illustrated in FIG. 2A is a signature array of a population of microparticles comprising the clusters of FIG. 1. The signature array comprises information about the counts of microparticles (Z-axis) within each distinct cluster of the population (oval dots). Each cluster is different from one another by at least one distinct discretely measurable common property P1 (X-axis) or P2 (Y-axis), or both P1 and P2. FIG. 2B is a signature array measured from a population of microparticles comprising ten (10) distinct clusters that are distinct from each other by at least size, infrared fluorescent intensity, and/or both, of the particles within each cluster.

The existence of a signature array for a population of entities provides a method of authenticating a product, for example a pharmaceutical product, which is easy to operate, but difficult to imitate or counterfeit. The method of authentication uses a product authentication code defined by a signature array of a population of entities, which has high per volume information content.

As used herein, a "product authentication code" or "product identification code" is a system that represents information specific to a product. The system or code is matched with a particular product or batch of products such that tacking or sampling of the code associated with the particular product or batch of products provides those individuals designated by the source originator of the code or the commercial user of the code to know any of a variety of characteristics or information about the product(s). For example, a "product authentication code" for a pharmaceutical product can represent information about the product, such as the chemical composition, the concentrations of the effective ingredients, the date or place of manufacture, the source of distribution, the batch, the shelf life, or a myriad of other information designations.

A "product authentication code" establishes the product's authenticity and provides a method for tracing the product in the supply chain. A "product authentication code" also addresses re-importation issues, e.g., where a product, for example an HIV drug, is sold outside the developed world under license conditions that preclude sale of licensed products back into the developed world. It can further be used in forensic toxicology to unequivocally identify use/misuse of a product and defend against baseless liability claims, etc.

It is readily appreciated that the present invention encompasses a vast number of product authentication codes depending on the number of clusters and the number of counts per cluster in the signature array. That is, varying the quantity or quality of entities within a population of entities results in a different signature array, thus a different product authentication code.

In some embodiments, different product authentication codes can be obtained by varying the combination of clusters of entities within the population of entities. Different clusters having different discretely measurable common properties are useful in creating different populations of entities, thus different signature arrays and different product authentication codes. For example, microparticles tagged with two different fluorescent dyes can be classified into different clusters based on different amounts of one or both of the two dyes. Various combinations of clusters of microparticles yield various populations of heterogeneous microparticles that can be used to encode various product authentication codes.

In other embodiments, different product authentication codes can be obtained by varying the counts of entities within clusters of the population of entities.

In yet other embodiments, different product authentication codes can be obtained by varying both the composition of clusters that form the population of entities and the counts of entities within one or more clusters.

It is readily appreciated that there is a high per volume information content within the signature arrays of this invention. Thus, the myriad of codes that may be encoded by these signature arrays is very great, limited only by Poisson counting statistics.

In one embodiment, entities with two discretely measurable properties, $P_1$ and $P_2$, can be classified into M clusters, as follows: $M=N_{P1} \times N_{P2}$, where N=number of discrete measurable levels for each property, $P_1$ or $P_2$. In general, the sum of all of the combinations of unique product authentication codes that can be created, I, from a data matrix of M clusters is: $I=2^M-1$, i.e., all possible combinations less the one instance where no cluster is represented in the array. In an illustrative embodiment, e.g., where $N_{p1}$ and $N_{p2}$ each=5, M=25 clusters of entities that can be obtained in this invention. From the 25 clusters, there are $I=2^{25}-1=33,554,431$ (i.e., approximately $3 \times 10^7$) possible unique product authentication codes generated by simply varying the combinations of the clusters to form the population of entities.

In another embodiment, R discretely measurable properties, $P_1, P_2, \ldots, P_R$, can be combined to yield a data matrix or data array with M clusters, as follows: $M=N_{P1} \times N_{P2} \times \ldots \times N_{PR}$, where N is as defined supra. Therefore, the sum of all the combinations of unique product authentication codes that can be created, I, from a data matrix of M clusters is $I=2^M-1$. Thus, with R=3 measurable properties and $N_{p1}$, $N_{p2}$, and $N_{p3}$ each equal to 5, M=125. Then, the number of possible unique product authentication codes is approximately $4 \times 10^{37}$.

In another embodiment, certain cluster(s) may be reserved to identify specific attribute(s) of the product, while other clusters in the population may be used in combination to create codes identifying attributes of the product that are expected to vary, such as production lot number. In this case, the sum of all the combinations of unique lot codes that could be generated from a data matrix of M clusters is: $I=2^{(M-K)}-1$, where K is the number of clusters always occupied or fixed for the product identifier. Thus, for a 25-cluster data array and where K is a set equal to 5, there are still 1,048,575 (i.e., approximately $1 \times 10^6$ or 1 million) possible unique lot identification codes.

In yet another embodiment, $C_{Ln}/C_{Ref}$, the ratio of count of entities within a cluster ($C_{Ln}$) relative to that within a reference cluster ($C_{Ref}$) or the absolute count of entities within a cluster, $[C_{Ln}]$, is used as a measured parameter, $P_C$. In the general case, $P_C$ expands the number of additional unique identifiers as follows: $I=(Nc+1)^{(M-K)}-1$, where $N_C$=number of statistically-distinguishable discrete ratios per cluster or absolute count levels that may be measured practically corresponding to a cluster, and M and K are as defined supra. Thus, from 25 clusters of entities, and where K is a set equal to 5 as above, 3 discrete ratios or absolute count levels for $N_C$ yields 1,099,511,627,775 (i.e., approximately $1 \times 10^{12}$ or 1 billion) possible unique lot identification codes.

In yet another embodiment, once the ratios for each cluster are specified, the total count of all entities per unit volume or unit weight of all clusters is used as a measured parameter, $P_{Tot}$. In the general case, $P_{Tot}$ expands the number of additional unique identifiers as follows: $I=N_{tot} \ast ((Nc+1)^{(M-K)}-1)$, where $N_{Tot}$=number of statistically-distinguishable discrete total count levels per unit weight or unit volume that may be measured practically summed across all clusters in a population of entities. Thus, from 25 clusters, where K is a set equal to 5, and 3 discrete ratios or absolute count levels for $N_C$ exist, as above, if $N_{Tot}$ has just 4 levels, more than 4 billion unique lot identification codes are possible.

In the foregoing embodiments, values selected for R, M, K, $N_C$, and $N_{Tot}$ are selected for purposes of illustration only, and are not meant to be limiting of the practical range of values that may be achieved for the corresponding parameters. That said, these examples demonstrate that signature arrays of a population of entities will accommodate a large amount of information.

One general aspect of the invention is a system that comprises information related to product authentication that is coupled to a quality control methodology. Information related to a product authentication code can be recorded, preferably stored in a database, and more preferably in a secured computer database. Information related to signature array can include, for example, the composition of the population of entities used to mark the product for authentication, the discretely measurable common properties of the distinct clusters of entities used to generate the signature array encoding the product authentication code, and optionally, the expected count or relative count of entities within each of the distinct clusters, etc. Information related to a product authentication code can include the information represented by the product authentication code, such as the chemical composition, the concentrations of the effective or active ingredients, the date or place of manufacture, the source of distribution, the batch number, or the shelf life, etc. Such information is readily retrievable, for example, by means of a computer operation. In a preferred embodiment, the system that comprises information related to product authentication is a computer.

Another general aspect of the invention is a method of marking a product for product authentication that is coupled to a quality control methodology, comprising the steps of: a) associating a population of entities with the product, wherein the population comprises at least two distinct clusters of entities having detectable counts or relative counts of entities per cluster; and b) assigning a signature array of the population of entities to the product as a product authentication code, wherein the signature array comprises information about the counts or relative counts of entities of at least two distinct clusters of entities within the population.

In a particular embodiment, the method of marking a product for product authentication that is coupled to a quality control methodology further comprises a step of correlating the count or relative count of entities within one or more clusters of the population with a specific piece of information about the product, such as the amount, concentration, or presence or absence of a product component.

As illustrated in Example 1 infra, in particular embodiments, fixed information about the product, such as the product identity, the concentration of the active ingredient, and the location of manufacture, etc., can be encoded by fixed array components using identical clusters at fixed counts or relative counts per cluster; and variable information about the product, such as lot number, date of manufacture, date of expiration, etc., can be encoded by variable array components using distinct clusters or identical clusters at distinct counts or relative counts of clusters. A signature array for a product authentication code can comprise a combination of fixed array component(s) and variable array component(s). Thus, distinct signature arrays encoding distinct product authentication codes can have partially identical array components (the fixed array components) and partially distinct array components (the variable array components). Populations of entities used for authenticating distinct products can share partially identical cluster compositions (to encode the fixed array components) and partially distinct cluster compositions (to encode the variable array components).

A wide range of entities are suitable for the present invention, so long as they are compatible with or non-deleterious to the product being marked. Examples of entities that can be used in the present invention, such as microparticles, nucleic acids molecules, or peptides/polypeptides, etc. are described supra.

The product marked can be solid, or semi-solid. However, this invention relates to marking of solid and semi-solid products in so far as it promotes quality control and product authentication. Examples of solid products include pharmaceuticals in tablets, capsules and powders; solid formulations of agrochemicals such as, but not limited to, insecticides, herbicides, fungicides and fertilizers; textiles and leather goods such as clothing and accessories; recordings such as audio and visual recordings including gramophone records, tape cassettes, floppy discs, video cassettes, memory cards, compact discs or other tangible forms of electronic information dissemination; electrical goods such as television sets, computers, DVD players, portable music devices, and radios; motor vehicle components and cameras; paper such as documents, confidential papers, notes, securities, labels, and packaging; chemical products such as inks, biocides, and rubbers; cosmetics such as creams; food products, and medical devices.

In one preferred embodiment of the invention, the marked product is a pharmaceutical product. The marking of a pharmaceutical product with a product authentication code of the invention can be useful to notify the user, dispenser and/or law enforcement personnel of the composition of the pharmaceutical product enabling the notified parties to determine if the product being tested is the genuine pharmaceutical product from the correct source in the correct concentration. The particles may be attached in or on to the articles to be authenticated through various means known in the art. Particle retention can be achieved using appropriate materials, for example, a mesh incorporated into the product or binding agents such as starches or sprays having adhesive properties.

It will be appreciated that the population of entities can be associated with the product in a wide variety of ways. The population of entities can be present in or on all or part of the coating of the product. The entities can be incorporated directly into the coating of the target product using any suitable technique.

In some embodiments when the entities are included in the coating of a pharmaceutical tablet, the entities are in the coating of the pharmaceutical product in an amount of below that is preferably about 0.1% (by weight) or less of the final tablet's total formulation weight. For example, where the entities are a population of microparticles, preferably the microparticles are included in the final coating formulation such that the total quantity of microparticles is less than 100 ppm, less than 50 ppm, less than 25 ppm, less than 10 ppm or less than 5 ppm of the total formulation composition.

In certain preferred embodiments where possible and where the entities are coated on a pharmaceutical product or medical device which has already been approved by a governmental agency that regulates pharmaceuticals (such as, for example, the Food and Drug Administration of the United States of America), the entities are included in an amount (e.g., such as an allowable impurity amount) which would not require a re-filing with, or re-approval by, the governmental agency of the pharmaceutical product or medical device that has been reformulated to include the heterogeneous population of microparticles. Preferably, the amount of the entities associated with the pharmaceutical composition is below the impurity level as provided by the International Conference on Harmonisation (ICH) guidelines.

In other embodiments when the entities are associated with a pharmaceutical formulation, the entities are ingestible and/or non-toxic in amounts used, and when associated with a coating of a medical device, the entities are biodegradable, biocompatible, and/or non-toxic.

In certain further embodiments, the entities can be associated with the product by being present in the product container, packaging or labeling, or a combination thereof. For example, the population of entities can be applied to the inner, outer, or both inner and outer portions of a container for the pharmaceutical product or medical device. The entities can be incorporated into the container during the manufacturing process of the container, and/or the entities can be applied to the inner and/or outer portions of the container or alternatively added during fill. According to this embodiment, the container can take any appropriate form.

In specific embodiments, the entities are included in a label or an article that can be affixed to the container containing the product. For example, where the entities are microparticles, inks containing the microparticles can be used to print the labeling directly onto the container, or printed dots can be printed directly onto the container. Alternatively, printed dots or inks containing the microparticles can be used to print the product authentication code onto a printable article or medium, which can be subsequently applied on a variety of interior and exterior surfaces of the product or the container of the product. Preferably, the printable article is adhesive. Inks, printable articles or media and methods to print microparticles onto a printable article or medium are know to those skilled in the art, see for example, U.S. Pat. No. 5,450,190.

Thus, in one aspect, the present invention relates to a method for minimizing the occurrence of packaging mismatch errors comprising the steps of: a) associating a population of entities with a product label to be applied to a container during a manufacturing process, wherein the population of entities comprises at least two distinct clusters of entities having detectable counts or relative counts of entities per cluster, wherein a signature array that comprises information about the counts or relative counts of entities of the at least two distinct clusters of entities is recorded; b) determining that the signature array is consistent with proper match between the label and the container; and c) rejecting labeled containers that are determined to be mismatched. Optionally, steps b and c are performed "on the fly" during a manufacturing labeling operation. Optionally, the container also incorporates a signature array for matching with the signature array of the label. Optionally, the container and or the label also incorporate machine-readable features (e.g., a bar code) for matching with any or all signature arrays.

In another aspect, the present invention relates to a method for minimizing the occurrence of packaging mismatch errors comprising the steps of: a) associating a population of entities with the bulk of a product prior to filling labeled containers during a manufacturing process, wherein the population of entities comprises at least two distinct clusters of entities having detectable counts or relative counts of entities per cluster, wherein a signature array that comprises information about the counts or relative counts of entities of the at least two distinct clusters of entities is recorded; b) determining that the signature array is consistent with proper match between the product bulk and the container; and c) rejecting filled containers that are determined to be mismatched. Optionally, steps b & c are performed "on the fly" during a manufacturing labeling operation. Optionally, step b is performed prior to step c, and no containers are filled if a mismatch is identified. Optionally, the container and/or the label also incorporate a signature array for matching with the bulk.

Regarding the avoidance of packaging mismatch, the current technology available today requires a specific code like 2D Data Matrix, Bar Code or Number/Letters to be printed on pressure sensitive labels or directly on containers (bottle, bag, jar, carton, leaflet, etc.). These printed codes are then read by scanners or vision systems on the production assembly line to verify the match between the label/component versus the product contents. The code to be printed and read by scanners or vision systems creates challenges of design and manufacturability, in that size, color, contrast, and position of the code impact its readability on a production line and aesthetics of the final package design.

The use of the signature array of the present invention does not require a specific size, position and contrast, and code information can cover a large surface of the label without compromising the product esthetics. For ease of application, this signature array can be integrated into the ink used for printing the label. Further, covering all or a large space on the label assures a wide range of field of view for scanners or vision systems to read the signature array, which enables faster reading on the production line. Additionally, there is greater flexibility in positioning scanners on the production line.

In yet another aspect, the signature array(s) of the present invention serve as authentication marks on and/or in finished products produced using the aforementioned methods for minimizing the occurrence of packaging mismatch errors.

The invention also includes an article that can be affixed to a product, wherein the article comprises a product authentication code of the invention.

For example, the entities can be microencapsulated into a layer of microcapsules, and then applied to the container containing a product. During microencapsulation, very thin coatings of inert natural or synthetic polymeric materials are deposited around the entities to form a layer of microcapsules. The coating material can be chosen from a number of natural and synthetic polymers that are non-reactive with the entities, and is preferably nontoxic. Other components such as surfactants and plasticizers, may also be added to microcapsules.

The entities can also be affixed on an integrated surface of a pharmaceutical product. For example, the entities can be printed or co-formulated into capsule material (any enteric); co-formulated in the coating of a tablet (e.g., an enteric coating); incorporated into the marking on pre-filled syringes (for injection); or printing on the outer layer of a patch (for a transdermal).

The product authentication code of the invention can be used in combination with one or more other means for product authentication, identification, or quality control. For example, it can be combined with authentication or identification methods, such as a radio frequency identification (RFID) tag, spectroscopic inks, hologram, reflective paper, laser etched paper, or a bar code on the package, container or label of the product. It can also be combined with a molecular marker or surface/formulated dye incorporated into the product. Additionally, where identification methods are used to track and manage pre-assembly, assembly and post-assembly manufacturing operations, the methods of the present invention can be used in combination.

Another general aspect of the invention relates to a product for sale in commerce, wherein the finished product comprises a product authentication code defined by a signature array of a population of entities associated with the product, wherein the signature array comprises information about the counts or relative counts of entities of at least two distinct clusters of entities within the population and wherein the product authentication code is coupled to a quality control methodology. In a preferred embodiment, the product is a pharmaceutical product.

Depending on the pre-definition or the coding information for the signature array, the array can be detected by measuring one or more discretely measurable properties of each and all entities within the population of entities, a representative number of entities within the population, or a specific set of one or more clusters of entities within the population.

Figure 3:
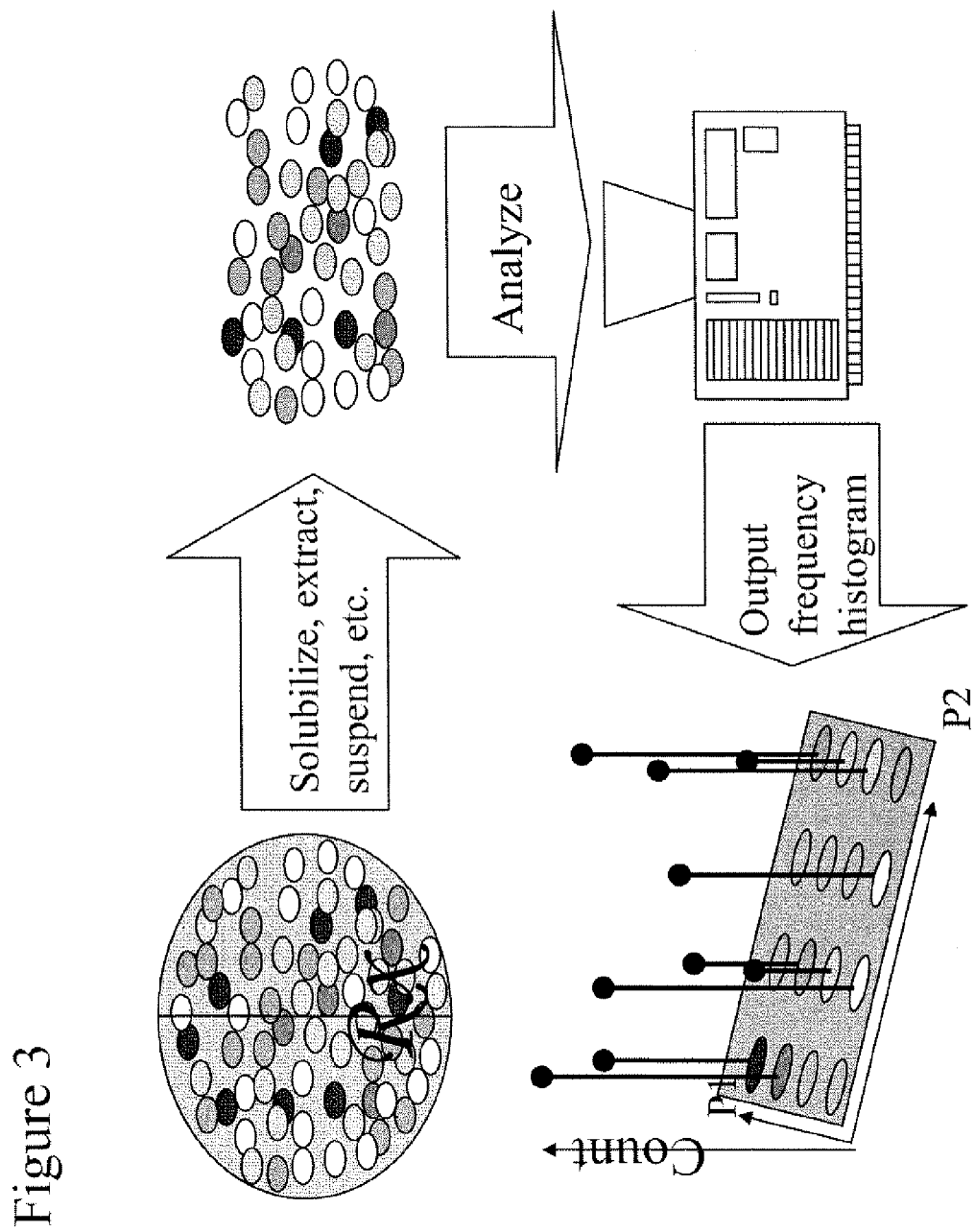
FIG. 3 is a flow chart of the steps for the measurement of the product authentication code of the invention.

In a specific embodiment as illustrated in FIG. 3, when the population of heterogeneous microparticles is incorporated into the coating of a solid product, the coating is first solubilized. Optionally the entire solid product can be solubilized. The microparticles within the product are extracted, dissolved or suspended in a solvent. The discretely measurable properties of microparticles can then be analyzed, for example, by using a flow cytometer or the like. Alternatively a static cytometer like the CELLSPOTTER® Analyzer from Immunicon can be used as the analyzing device. Preferably, the analyzing device (analyzer) is small and handheld. The analyzer can measure the discretely measurable properties of the microparticles, plot the measured properties in a signature array, and preferably compare the signature array with a saved expected value or values.

In certain embodiments of the present invention, the discretely measurable properties of the entities can be measured in the presence of the product. For example, when the population of heterogeneous microparticles is incorporated into a coating, the fluorescent intensity of the fluorescent tag associated with the microparticle or the particle size of the microparticle can be measured directly by a reader system as is described in US20050100204 the disclosure of which is hereby incorporated by reference.

In a typical reader, UV light is used to trigger the fluorescence of the microparticles. A "BLOB" of an area of the product where the individual fluorescent microspheres are located is used to capture all the microparticles' colors, identify and quantify the gradients of each color detected, as well as the density (for amplitude) of the pigmentation of the microparticles. To ensure repeatability, the reader/vision system is first calibrated with a specific color calibration using a color standard. Currently, "BLOB" function offers similar capability by returning percentage of colors (for RGB in percentage) of the pixels inside the area located in the "BLOB". BLOB stands for "Binary Large Object". As generally understood in the art, a blob is a collection of binary data stored as a single entity in a database management system. Blobs are typically images, audio or other multimedia objects, though sometimes binary code is stored as a blob. In this case, it is the collection of images stored in a vision system's internal memory (data base) to enable binary analysis to trigger specific context based visualization on the configuration of the BLOB ANALYSIS TOOL of the vision system.

A preferred reader, scanner, camera or vision system of the present invention would be capable of detecting UV. Such scanners/readers are readily available in the market place from companies such SICK (scanners), MICROSCAN (scanners) COGNEX/DVT (Vision) as well as SIEMENS (Scanners and Vision).

The preferred analyzer can measure the discretely measurable properties of the microparticles, plot the measured properties in a signature array, and preferably compare the signature array with a saved expected value or values. Those of ordinary skill in the art will recognize that a reader system as is described in US20050100204, is used by way of example only, because it can be applied to assess information associated with the entities of the present invention. The skilled artisan will also recognize that there are a variety of methods to assess information associated with the entities of the present invention.

In some embodiments, the method of the invention further comprises a step of collecting some or all of the population of entities, such as the microparticles. In one embodiment, when the microparticles are associated with the label or container of the product, the microparticles can be collected by many standard techniques. For example, they can be rinsed off the container or label. In the case where the microparticles are microencapsulated into a layer of microcapsules, the layer of microcapsules can be peeled off from the label or container and dissolved or reconstituted, if necessary, to release the encapsulated microparticles. In a specific embodiment, the population of heterogeneous microparticles is incorporated into a coating that is soluble in aqueous solvents.

The microparticles can also be collected by specific properties associated with the microparticles, such as the physical or chemical characteristic of the particles, magnetic, lipophilic, hydrophobic, or charge property of the particles. In a particular embodiment, WO2004063752 discloses a method for separating or quantitatively determining target particles in a sample. The method changes the amount of charge on the surface of the particles and utilizes the changed charge for separation and quantitative determination of the particles. Such a method can be used in the present invention to collect the microparticles that are incorporated into the product. The preceding relates to the instant invention to the extent that coating QC can be effected destructively if according to a reasonable sampling plan.

In some situations, microparticles tend to form agglomerates when being mixed into a liquid. Effective means of deagglomerating and dispersing can be used to overcome the bonding forces among microparticles after wetting or reconstitution. Such means include, but are not limited to, deagglomerating treatment with ultrasound, rotor stator mixers (e.g. ultra turrax), piston homogenizers, gear pumps or beat mills, colloid mills or ball mills. Again, the preceding does relate to the instant invention to the extent that coating QC can be effected destructively if according to a reasonable sampling plan.

In some embodiments, multiple discretely measurable properties of the entities within a population can be measured by a single measurement. For example, the discretely measurable properties of each microparticle within the population, such as the intensity of a dye, including a fluorescent dye associated with the particle, the number of particles, or the particle size of particles, can be obtained using the reader system as is described in US20050100204. The measured properties can then be plotted using readily available computer software programs.

The simultaneous measurement of two or more discretely measurable properties of the entities is preferred when there is a concern that other components present in the environment of the entities may interfere with the specific measurement of the discretely measurable properties of the entities. For example, where the reader system as is described in US20050100204, the measurement is set to detect the size of particles having a certain fluorescent tag, the interference from the formulation components is minimized because the formulation components lack the fluorescent tag and will not be measured.

Those of ordinary skill in the art will recognize that populations of heterogeneous entities can be labeled with tags that can be measured with acceptable levels of interference from coating formulation components, that can be separated from interfering product components by convenient means, or that have a combination of the forgoing properties.

The discretely measurable properties of the entities can be measured by methods known to those skilled in the art. For example, laser scanning cytometry or flow cytometry is routinely used for simultaneous measurement of multiple properties of a microparticle, such as the size or shape of the particle, or fluorescence signals derived from a fluorophore or plurality of fluorophores associated with the particle. Flow cytometry is applicable to cases where, further to a QC sample plan, the microparticles are first eluted from the surface coating of the pharmaceutical product and subjected to cytometric analysis.

In flow cytometry, particles are introduced into the center of a fast moving fluid stream and forced to flow single file out a small diameter orifice at uniform speeds. The particles are hydrodynamically focused to the center of the stream by a surrounding layer of sheath fluid. The particles within the stream pass a measurement station where they are illuminated by a light source and measurements can be made at rates of $2.5 \times 10^2$ to $10^6$ particles per minute. Laser light sources are used in the measurement of particles. Typical laser light sources used include argon ion lasers (UV, blue and green light), krypton lasers (yellow and red light), helium-cadmium lasers (UV and blue light), and helium-neon lasers (red light).

A preferred flow cytometer is capable of selecting for the detection of target-correlated signal associated with particles having a defined range of forward-angle and right-angle scattering signal intensity or particular fluorescence (see for example, Yang, et al. *Blood* 81, 1083 (1993), Barker et al. *Blood* 83, 1079-1085 (1994), Fulton et al., *Clin Chem* 43:1749-56(1997), Fulwyler et al., *Methods Cell Biology* 33: 613-29 (1990), and McHugh, *Methods Cell Biology*, Second Edition, Academic Press, v 42, 575 (1994)). Data acquisition is initiated by light scattering and/or fluorescence associated with a particle. Selecting for signal associated with a particle enables the detection of target-correlated signal without interference from fluorescence originating from the bulk solution phase in which the particles are immersed. Thus, the signal/noise ratio is large. Target-correlated signal is proportional to the amount of target, and determination of multiple target nucleic acids is also possible using the preferred flow cytometric methods. Multiplex analysis of nucleic acids that are free in solution using flow cytometry has been described, see for example, by Fulton et al. (1997), supra, and Fulwyler et al. (1990), supra.

The discretely measurable properties of entities can also be measured by methods utilizing a microscope. Microparticles can be examined manually under a microscope, using a "holder" such as a slide, a hemacytometer chamber, or a Nageotte chamber (also a volumetric analysis). Indeed, many pharmaceutical products have size specifications that were first laid down using microscopy. A typical specification would be for 95% of particles to be less than a specific size (e.g. 50 microns). This would be tested by a skilled technician dispersing a sample on a slide then counting microparticles against a calibrated eye piece reticle.

Microparticles can also be examined automatically or semi-automatically using a static cytometer by scanning. Here the objective field is moved over a fixed stage or using an automated stage, wherein the field is moved past a fixed objective. An example of a static cytometer is the CELL-SPOTTER® Analyzer from Immunicon (a semi-automated fluorescence microscope that enumerates and differentiates between the immuno-magnetically selected microparticle based on fluorescence signals).

The discretely measurable properties of entities can also be measured using a COULTER COUNTER. In a COULTER COUNTER chamber, entities like microparticles suspended in a weak electrolyte solution are drawn through a small aperture separating two electrodes between which an electric current flows. The voltage applied across the aperture creates a "sensing zone". As each entity passes through the aperture (or "sensing zone") it displaces its own volume of conducting liquid, momentarily increasing the impedance of the aperture. This change in impedance produces a tiny but proportional current flow into an amplifier that converts the current fluctuation into a voltage pulse. The Coulter Principle states that amplitude of this pulse is directly proportional to the volume of the entity that produced it. Scaling these pulse heights in volume units enables a size distribution to be acquired and displayed. In addition, if a metering device is used to draw a known volume of the particle suspension through the aperture, a count of the number of pulses will yield the concentration of entities in the sample. The COULTER COUNTER technology can be coupled with optical detection of flow cytometry.

In further embodiments, instruments used for analysis of cells can be adapted to measure the discretely measurable properties of entities using flow cytometry or COULTER COUNTER technology. Such instruments, include, but are not limited to Beckman-Coulter Z1™ Series COULTER COUNTER® Cell and PARTICLE COUNTER (Beckman Coulter, Fullerton, Calif.); PARTEC CYFLOW® SL (Partec, Münster Germany); and Guava Personal Cell Analysis (PCA) System (Guava Technologies, Hayward, Calif.).

Other types of technologies that can be used to measure the discretely measurable properties of entities include the particle counters and particle sizers that are commercially available from Particular Sciences (Dublin, Ireland). "Particle Counters" are the instruments that count entities that are present in a given sample (usually by volume or weight). In contrast, most "Particle Sizers" detect entities present over wide size ranges and return the relative percentages of events within specified size intervals. The discretely measurable properties of entities can be measured using air particle counters with laser detection systems, which are used in clean rooms and hospitals to test the levels of particles from about 0.3~10 microns to certain standards (class 10, 100 etc); or liquid particle counters with light obscuration detectors, which are used in the micron size range and frequently used to test to standards (USP). Laser sensors enable one to count particles below a 1 micron limit. Liquid counters are used with aqueous samples, injectables and with oils used in industry. More detail is obtainable from the company web site of Particle Measuring Systems, Inc (Boulder, Colo.).

One other general aspect of the present invention is a method of authenticating a product, comprising the steps of: a) associating a population of entities with the product, wherein the population comprises at least two distinct clusters of entities having detectable counts or relative counts of entities per cluster; b) assigning a signature array of the population of entities to the product as a product authentication code, wherein the signature array comprises information about the counts or relative counts of entities of at least two distinct clusters of entities within the population; wherein information about the signature array and the product authentication code is recorded; c) analyzing the product to obtain a measured signature array of the population of entities associated with the product; d) comparing the measured signature array with that which is expected based on the recorded information; and e) accepting the product as authenticate when the measured signature array matches that which is expected.

The authentication method begins with marking a product with a product authentication code of the present invention. The information associated with the product authentication code and the information about the particular signature array that encodes the product identification code is recorded. Based on the recorded information, an authorized person would expect to find a certain signature array based on certain product information, or certain product information based on the detection of a certain signature array associated with the product. To confirm whether a product in commerce is authentic, an authorized person, based on knowledge from the record, will readily know what particular signature array is expected to be detected from the product. After determining the signature array associated with the product using methods described supra, the authorized person will compare the measured signature array with what is expected based on the recorded information. A match of the measured signature array with that which is expected, taking into account of the experimental errors of the measurements, indicates that the product in commerce is authentic.

The experimental errors of the measurement can result in uncertainty about whether the measured signature array indeed matches expected values. To increase the level of confidence, multiple signature arrays may be associated with a single product, optionally, at, on or within different portions of the product to allow multiple measurements and comparisons of the measured signature arrays with expected values. The multiple signature arrays can be identical or distinct.

In an illustrative embodiment, even a simple miscoating of the product can be detected by the reduced microparticle count per unit surface area of microparticles associated with the product to form a signature array.

Because a product authentication code of the invention can encrypt product (or active ingredient) concentration information, the product authentication code can be used as a surrogate for direct analytical measurement, eliminating costly analytical steps in manufacturing quality control. Therefore, the invention also provides a method for quality control and release of products from a manufacturing process, comprising the steps of: a) associating a population of entities with a product during the manufacturing process, wherein the population of entities comprises at least two distinct clusters of entities having detectable counts or relative counts of entities per cluster, wherein a signature array that comprises information about the counts or relative counts of entities of the at least two distinct clusters of entities is recorded; b) analyzing the product to obtain a measured signature array of the population of entities associated with the product; c) comparing the measured signature array with that which is expected based on the recorded information; and d) releasing products manufactured by the manufacturing process when the measured signature array matches that which is expected. In a preferred embodiment, the product is a pharmaceutical product.

In a particular embodiment, the population of entities or a cluster of the population is incorporated into an ingredient or component of the product coating during the manufacturing process. Thus, the presence of the expected signature array or information about the cluster detected from the product is indicative of the presence and quantity of the ingredient or component in the product.

The invention further includes a product manufactured by the process of manufacturing using the product authentication code as a surrogate for direct analytical measurements.

This invention will be better understood by reference to the examples that follow. Those skilled in the art will readily appreciate that these examples are only illustrative of the invention and not limiting.

EXAMPLE 1

Authenticating Solid Formulations Using Fluorescent Microparticles Applied to the Product Surface In the present Example 1, the signature array of heterogeneous fluorescent microparticle entities was associated with a pharmaceutical product by application of a coating to the surface of an insoluble tablet formulation, wherein the microparticles used were of two different sizes and labeled with either the same or two different fluorescent dyes. A person skilled in the art can readily appreciate that other coatings for pharmaceutical tablet can be used and that other types of entities can also be used following similar procedures to those of this example.

Tablets were prepared from calcium phosphate (CaPO$_4$; Fuji Chemical) with a sucrose coating in a three-step process: manufacturing of tablets, sugar coating of tablets and application of microbeads. The coating process was performed in a 6-inch pan coater. The first step of the sugar coating process was to pre-condition the coater. This was accomplished by placing a quantity of placebo (microcrystalline cellulose) tablets sufficient to fill the coater for pre-conditioning. Excess sucrose solution was added and the pan rotated until the sides of the coating pan were adequately covered in sucrose. A spatula was used as needed to ensure that the coater was sufficiently covered. The tablets and excess sucrose were discarded and the remaining sucrose in the coating pan was dried. Tablets comprising of dibasic calcium phosphate (FUJICALIN) with magnesium stearate were added to the pre-conditioned coater. These tablets were manufactured using deep concave tooling to make an almost spherical tablet. A small amount of sucrose solution was added to coat the tablets and then they were dried with alternating room temperature air and hot air while rotating in the coating pan. This process was repeated until the tablets were adequately covered with sucrose and dried. The microbead suspension was then mixed using a vortex to obtain a uniform suspension. A measured quantity of the microbead suspension was applied to the surface of individual tablets and dried at room temperature.

Microparticles labeled with fluorescent dyes purchased from Invitrogen Corporation (Carlsbad, Calif.). Individual vials of microparticles from LINEARFLOW flow cytometry intensity calibration particle kits were obtained as follows: Deep Red 2.5 μm (L14818; lot #38976a), Deep Red 6 μm (L14819; lot #39308a), Green 2.5 μm (L14821; lot # 21833w), and Green 6 μm (L14822; lot #41635a). These particles were labeled by the manufacturer with different dyes: a fluorescent dye at 633 nm excitation/660 nm emission (Deep Red, Dye1) and a fluorescent dye at 488 nm excitation/515 nm emission (Green, Dye 2) respectively. Each kit contained six vials of polystyrene particle suspensions stained with the corresponding dyes at different intensity levels that were visualized as six discrete peaks on a fluorescence histogram when analyzed using a Becton Dickinson FACSCALIBER flow cytometer and CELLQUESTPRO analysis software.

The microparticles were formulated to yield signature arrays that would match some or all of the values shown in the "Input" column of Table 1, which is the percent of total fluorescent events per fluorescence detector channel on the FACSCALIBUR flow cytometer. Microparticles with "G" events were detected in the FL1 channel and "R" events in the FL2 channel. The signature array of each of the G and R populations was designed to match half of the input values. Thus, the signature array of the G+R population, which was a mixture of the G and R population in equal volume, would match all of the input values.

Each of the G, R, and G+R populations was mixed 5:1 with a solution of saturated sucrose. Six microliters of each mixture was applied to the sucrose-coated surface of an individual test tablet, and left to dry overnight in the dark under ambient conditions. To reveal a characteristic visible mark on the tablet within the simulated logo, the tablets were examined under ultraviolet light. It was observed that tablets applied with G, R, and G+R populations fluoresced visibly in characteristic green, red, and orange light, respectively.

To reveal the underlying signature array information, the tablet was washed with 400 μl DPBS into 1.5 ml microfuge tubes and then centrifuged for 10 minutes at 14,000 rpm in a microfuge. The supernatant was removed from each tube by aspiration until approximately 50 μl fluid remained. One hundred fifty microliters of fresh DPBS/0.1% triton X100 was added back to each sample prior to transfer into separate 12×75 mm polystyrene tubes (FALCON) for FACS. As shown in Table 1, the measured signature arrays corresponding to G, R, and G+R populations matched half or all of the Input values.

TABLE 1

Signature arrays that matched some or all of the Input values

|  | Input | G + R | G | R |
|---|---|---|---|---|
| Green - B | 38.3 | 37.7 | 43.5 | 0.0 |
| C | 9.1 | 8.3 | 7.5 | 0.0 |
| D | 3.5 | 3.9 | 3.3 | 0.0 |
| E | 32.6 | 34.5 | 31.4 | 0.0 |
| F | 16.6 | 15.6 | 14.1 | 0.0 |

TABLE 1-continued

Signature arrays that matched some or all of the Input values

|   | Input | G + R | G | R |
|---|---|---|---|---|
| Red - B | 26.5 | 27.7 | 0.0 | 27.8 |
| C | 36.0 | 36.3 | 0.0 | 34.5 |
| D | 8.8 | 9.1 | 0.0 | 9.8 |
| E | 5.8 | 5.1 | 0.0 | 5.6 |
| F | 22.9 | 21.8 | 0.0 | 22.3 |

To test the reproducibility of associating a signature array by the methods of this Example, the population G2/R2 as described in Table 2b of Example 2 was formulated, and mixed 5:1 with a solution of saturated sucrose. Six microliters of said mixture was applied to the sucrose-coated surface of each of six test tablets, then left to dry overnight in the dark under ambient conditions. Three tablets were then washed with 400 µl DPBS per tablet into 1.5 ml microfuge tubes. The other three tablets were washed with 400 µl DPBS/0.1% triton X100. Next, the samples were prepared for FACS analysis as described above.

Figure 4:
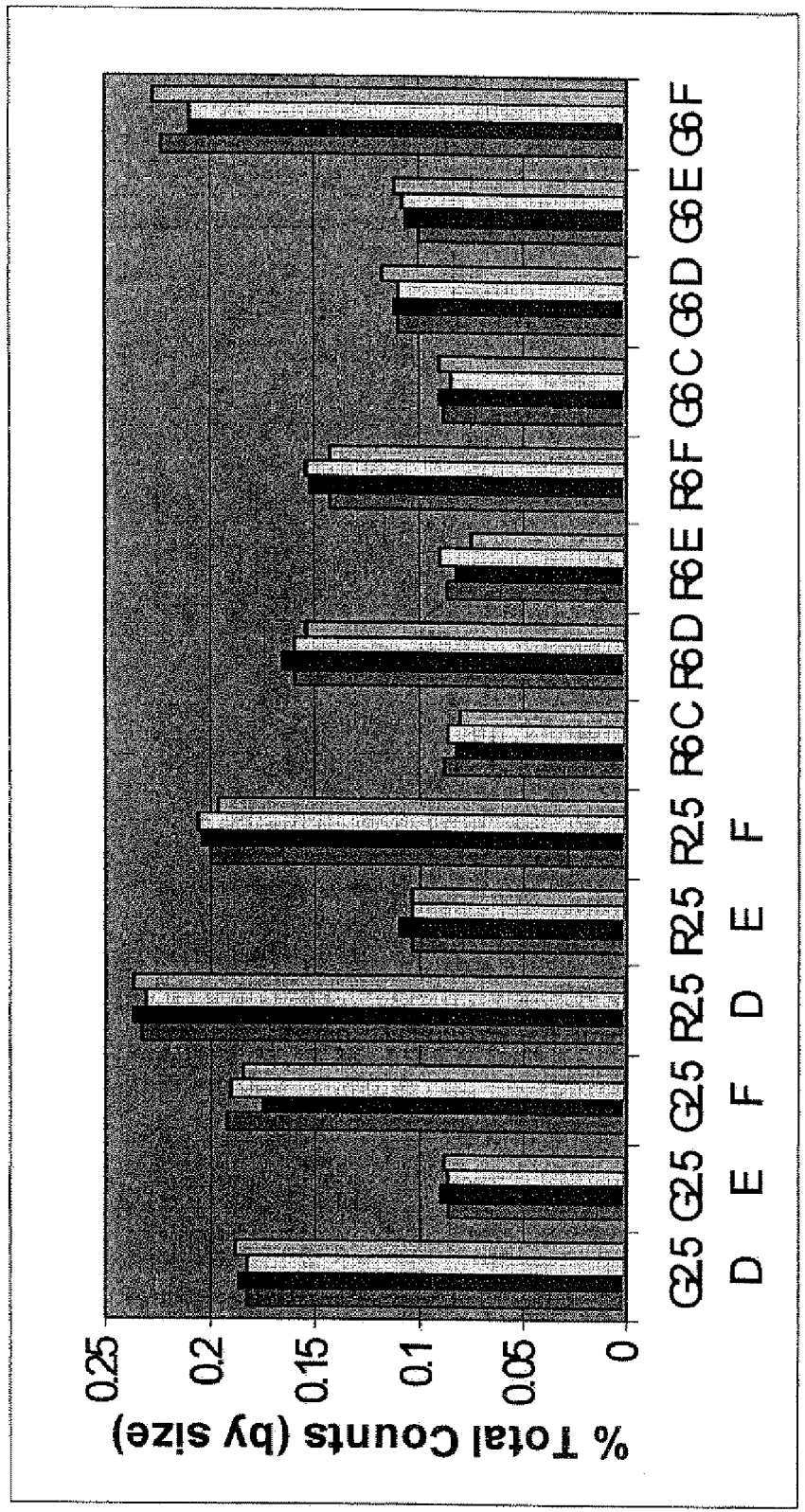
FIG. 4 shows that the signature array measured from a tablet marked with the population G2/R2 on the surface of the tablet matched the expected array.

FIG. 4 shows that the signature arrays measured from the solid formulation containing the population G2/R2 after washing with DPBS matched that from the controls consistently. Listed in the X-axis are the 14 distinct clusters within the G2/R2 population. For each cluster, the first three bar plots from the left represent the relative counts of entities measured from the three tablets; and the fourth bar plot represents the relative counts of entities measured from the G2/R2 population directly, i.e., the population incorporated directly into PBS as a control. The relative count is defined as the count of entities per cluster relative to the sum of counts of entities having the same size, i.e., 2.5 µm or 6 µm.

This Example 1 demonstrates that a signature array can be associated with an article of product by deposition on the article's surface in a way such that both a visible authenticating mark and an invisible signature array can be revealed. Such a signature array can be associated with a logo or other visibly identifying mark, which are commonly placed on the surface of commercial pharmaceutical products. This Example 1 further illustrates that the measurement of the signature array can function as a manufacturing quality control parameter, either as a binary indicator of coating or failing to coat a unit of product, or quantitatively as a surrogate for directly determining the quantity of material deposited in a coating. Those of ordinary skill in the art of pharmaceutical sciences recognize that the visible component is not required to achieve association of the signature array using modifications of the method of this Example.

EXAMPLE 2

Counts of Entities Correlate with the Deposition of a Coating Sprayed on a Stent This Example illustrates a process for making a product using attributes of the signature array of the present invention wherein counts of entities within sets of clusters correlate with the deposition of a coating sprayed on a stent, while maintaining all of the benefits that said array has for authenticating the product. Particularly, this Example demonstrates a process that is useful for monitoring the deposition of a drug coating sprayed on stent, such as, for example, the CYPHER® Sirolimus-eluting Coronary Stent. CYPHER® provides a metal scaffold to open a blocked artery and a coating of the anti-rejection-type medication, sirolimus, that helps limit the overgrowth of normal cells while the artery heals, reducing the chance of re-blockage in the treated area. It is understood by one of ordinary skill in the art that this method or obvious adaptation of it can be applied to other coated manufactured articles.

Polystyrene microparticles sold as LINEARFLOW flow cytometry intensity calibration particle kits were purchased from Invitrogen Corporation (Carlsbad, Calif.). Individual vials of microparticles from the following kits were used as a heterogeneous population of entities: Deep Red 2.5 µm (L14818; lot #38976a), Deep Red 6 gm (L14819; lot # 39308a), Green 2.5 µm (L14821; lot #21833w), and Green 6 µm (L14822; lot #41635a). These particles were supplied by Invitrogen with different dyes: a fluorescent dye at 633 nm excitation/660 nm emission (Deep Red, Dye 1) and a fluorescent dye at 488 nm excitation/515 nm emission (Green, Dye 2) respectively. The three individual vials with the highest fluorescence intensity within the 2.5 µm sets (Invitrogen designation vials "D", "E", and "F") and the four individual vials with the highest fluorescence intensity within the 6.0 µm sets (Invitrogen designation vials "C", "D", "E", and "F") were used as clusters of entities to prepare heterogeneous populations of entities according to the volumes given in Table 1.

Those skilled in the art recognize that a bioabsorbable microparticle of similar size and labeled with non-toxic dyes are preferred to replace these polystyrene microparticles in applications where stents are to be implanted in human subjects. The two factors that drive choice of a size range are detectability and safety; smaller being preferred. Polystyrene microparticles were used in this example for illustrative purposes and because they are compatible with a handy detector device (flow cytometer) and available commercially. The primary set of desirable properties for preferred microparticles are biocompatibility with the organs and systems with which the product will contact, i.e., there is lower stringency for a label in an enteric coating that will pass in stool compared to a stent coating that will desorb during the implanted device's lifetime. Additional important features are solvent and chemical resistance, low surface energy and low protein adsorption, elastomericity (allowing for application performance), and ease with which the materials can accommodate multiple dyes and/or discrete physical features. See for example: Larken E. Euliss, Julie A. DuPont, Stephanie Gratton and Joseph DeSimone; Imparting size, shape, and composition control of materials for nanomedicine (pdf), Chemical Society Reviews First published as an Advance Article on the web Sep. 20, 2006. Jason P. Rolland, Benjamin W. Maynor, Larken E. Euliss, Ansley E. Exner, Ginger M. Denison, and Joseph M. DeSimone Direct Fabrication and Harvesting of Monodisperse, Shape-Specific Nanobiomaterials (pdf), JACS Mar. 28, 2005. Jason P. Rolland, Erik C. Hagberg, Ginger M. Denison, Kenneth R. Carter, and Joseph M. DeSimone; High-Resolution Soft Lithography: Enabling Materials for Nanotechnologies (pdf), Angewandte Chemie, Nov. 5, 2004

TABLE 2a

Populations of Invitrogen LINEARFLOW flow cytometry intensity calibration microparticles comprising 7 clusters

|   | G1 (µl) | R1 (µl) | G2 (µl) | R2 (µl) |
|---|---|---|---|---|
| 2.5 µm Suspension D | 100 | 100 | 200 | 200 |
| 2.5 µm Suspension E | 200 | 200 | 100 | 100 |
| 2.5 µm Suspension F | 100 | 100 | 200 | 200 |
| 6 µm Suspension C | 200 | 200 | 100 | 100 |

TABLE 2a-continued

Populations of Invitrogen LINEARFLOW flow cytometry intensity calibration microparticles comprising 7 clusters

|  | G1 (µl) | R1 (µl) | G2 (µl) | R2 (µl) |
|---|---|---|---|---|
| 6 µm Suspension D | 100 | 100 | 200 | 200 |
| 6 µm Suspension E | 200 | 200 | 100 | 100 |
| 6 µm Suspension F | 200 | 200 | 200 | 200 |
| Total Volume | 1100 | 1100 | 1100 | 1100 |

TABLE 2b

Populations of Invitrogen LINEARFLOW flow cytometry intensity calibration microparticles comprising 14 clusters prepared from combinations of 7-cluster arrays described in Table 2a.

|  | G1/R1 (µl) | G1/R2 (µl) | G2/R1 (µl) | G2/R2 (µl) |
|---|---|---|---|---|
| G1/R1 | 400 | 400 |  |  |
| G1/R2 | 400 |  | 400 |  |
| G2 |  |  | 400 | 400 |
| R2 |  | 400 |  | 400 |
| Total Volume | 800 | 800 | 800 | 800 |

G = LINEARFLOW Green particles (2.5 µm @ 4.6e10$^7$ particles/ml; 6 µm @1.9e10$^7$ particles/ml).
R = LINEARFLOW Deep Red particles (2.5 6 µm @ 4.6e10$^7$ particles/ml; 6 µm @ 2.1e10$^7$ particles/ml).

G=LINEARFLOW Green particles (2.5 µm @4.6e10$^7$ particles/ml; 6 µm @1.9e10$^7$ particles/ml).
R=LINEARFLOW Deep Red particles (2.5 6 µm @4.6e10$^7$ particles/ml; 6 µm 2.1e10$^7$ particles/ml). Each of the populations of microparticles according to Table 2b, G1/R1, G1/R2, G2/R1, and G2/R2, contain 14 distinct clusters of entities, but each is a unique signature array.

A combination of two polymers, 67% polyethylene-co-vinyl acetate (PEVA) and 33% poly n-butyl methacrylate (PBMA), is mixed with sirolimus to make up the basecoat formulation sufficient for application to approximately 1000 stents. Each of the four arrays (G1/R1, G1/R2, G2/R1, and G2/R2) were mixed into separate fractions of this basecoat formulation such that a minimum of 50,000 total microparticle counts is contained in the volume of basecoat formulation that is required to be applied to each stent.

In accordance with a prescribed manufacturing process, bare metal stents were treated with parylene C. Fifty treated stents were spray coated for a period of time (X minutes) such that the required amount of the G1/R1 labeled drug/polymer basecoat formulation coating adheres to the entire surface (i.e., luminal and abluminal) of the stent. Groups of 50 treated stents were similarly treated with each of G1/R2, G2/R1, and G2/R2 labeled drug/polymer basecoat formulation coating. To simulate a manufacturing coating process deficiency, treated stents were spray coated for half the above period of time (X/2 minutes) such that half the required amount of the G1/R1 labeled drug/polymer basecoat formulation coating is adhered to the entire surface of the stent. Groups of fifty treated stents were spray coated for X/2 minutes with each of G1/R2, G2/R1, and G2/R2 labeled drug/polymer basecoat formulation coating. A drug-free topcoat of PBMA polymer was applied to all of the groups of stents, as would normally be included in the manufacturing process to control the release kinetics of sirolimus after stent implantation.

The total microparticle counts and the membership within microparticle clusters was determined for each stent from each group by measuring the microparticle counts on the surface of the stent as it rotates past a measurement instrument, and results are shown in Table 3.

TABLE 3

Signature array counts correlate with the deposition of a coating sprayed on a stent

| Signature ID | Mean Total Count | | Meets Release Criteria |
|---|---|---|---|
| Coating time = X | | | |
| G1/R1 | Confirmed | ~100% Expected | Yes |
| G1/R2 | Confirmed | ~100% Expected | Yes |
| G2/R1 | Confirmed | ~100% Expected | Yes |
| G2/R2 | Confirmed | ~100% Expected | Yes |
| Coating time = X/2 | | | |
| G1/R1 | Confirmed | ~50% Expected | No |
| G1/R2 | Confirmed | ~50% Expected | No |
| G2/R1 | Confirmed | ~50% Expected | No |
| G2/R2 | Confirmed | ~50% Expected | No |

Those of ordinary skill in the art of pharmaceutical sciences recognize that a similar method as that described in this Example 2 may be employed for quality control and release testing of many processes used to coat solid supports of many types. Additionally, it is evident to the skilled practitioner that this Example 2 allows for the methods of this invention to substitute for other costly and or more complicated analytical methods that might otherwise be used to assure such coatings. Also, the method of the present invention can be performed "in-line" thereby allowing for real time monitoring of the coating process, thereby avoiding that the manufactured batch to be placed on hold awaiting release results, and should a problem be identified, the entire batch is not affected.

EXAMPLE 3

Detecting an Expected Code Indicates Proper Mixing of Components that are Deposited on a Hemostatic Sponge by Immersing the Sponge This Example illustrates a process for making a product using attributes of the signature array of the present invention to determine proper mixing of components to be deposited on the solid matrix of a product, while maintaining all of the benefits that said array has for authenticating the product. Particularly, this Example demonstrates a process that would be useful for manufacturing a hemostatic sponge by immersing the sponge in a bath in order to coat the sponge with a biologically active component.

A hemostatic sponge has, for example, a solid matrix support comprising a woven mesh of bioabsorbable materials, such as polydioxanone or polyglactin 910 found in PDS II or VICRYL sutures, respectively, that is coated with the hemostatic proteins, thrombin and fibrin. For the purpose of illustration, it is assumed that a step in the manufacturing process is to combine two separate non-aqueous suspensions of the proteins thrombin (Portion A) and fibrin (Portion B) in a 9 parts labeled Portion A to 1 part labeled Portion B ratio. A subsequent step is to immerse the solid matrix support (in the non-aqueous suspension?), and product quality control release is dependent upon proper mixing of the suspensions and adequate uniform coating of the sponge after removal from the immersion and drying.

Populations of fluorescent microparticles from Invitrogen Corporation as described in Example 1 above were prepared by mixing the quantities shown in Table 4. Sub-population Y was added to Portion B at effectively 10× the dilution (i.e., 250 μl of Sub-population Y per 1 ml Portion B) that Sub-population X was added to Portion A (i.e., 25 μl of Sub-population X per 1 ml Portion A), such that when 3 replicates are made of 9 parts labeled Portion A plus 1 part labeled Portion B, the following target ratio is empirically determined by thoroughly vortexing the samples and determining relative cluster membership by fluorescence flow cytometry:
Ratio=(Total counts obtained for all clusters in Sub-population Y)/(Total counts obtained for all clusters in Sub-population X).

TABLE 4

Populations of Invitrogen microparticles for product quality control and release testing

| | Sub-Population X (μl) | | Sub-Population Y μl) |
|---|---|---|---|
| Green 2.5 μl suspension D | 100 | Deep Red 2.5 μl suspension D | 200 |
| E | 200 | E | 100 |
| F | 100 | F | 200 |
| Green 6 μl suspension C | 200 | Deep Red 6 μl suspension C | 100 |
| D | 100 | D | 200 |
| E | 200 | E | 100 |
| F | 200 | F | 200 |
| Total Volume | 1100 | Total Volume | 1100 |

To simulate both the proper manufacturing process and potential mixing manufacturing errors, a constant volume of Portion A was mixed with varying amounts of Portion B according to the ratios listed Table 5. Thus, in addition to the correct 9:1 ratio, three cases were simulated wherein the addition of the active ingredient fibrin was incorrectly low (Trials 2, 3 and 4) and three cases were simulated wherein said addition was incorrectly high (Trials 6, 7, and 8). Also included was a simulation of inadvertent failure to add any of Portion B (Trial 1).

TABLE 5

Simulation of the manufacturing process addition error

| Trial # | Portion A | Portion B |
|---|---|---|
| 1 | 9 parts | None |
| 2 | 9 parts | 0.5 parts |
| 3 | 9 parts | 0.75 parts |
| 4 | 9 parts | 0.875 parts |
| 5 | 9 parts | 1 part |
| 6 | 9 parts | 1.125 parts |
| 7 | 9 parts | 1.25 parts |
| 8 | 9 parts | 1.5 parts |

In accordance with proper manufacturing process, three replicate coatings were achieved with each Trial suspension by immersing a single solid matrix support in each replicate case for a fixed time and at a temperature (T1) such that the required amount of the labeled Portion A/Portion B suspension was adhered at specified density to the support surface. To simulate a manufacturing deficiency, three replicate coatings wee achieved with each Trial suspension by immersing a single solid matrix support in each replicate case for a fixed time and at a temperature (T2) such that half required amount of the labeled Portion A/Portion B suspension was adhered to the support surface versus the specified density.

To simulate quality control release testing of the coated solid supports, the total microparticle counts and the membership within microparticle clusters was determined for each sponge from each group by using a measurement device that is installed at the last station of the manufacturing line and results are shown in Table 6. For the purposes of this simulation, coatings determined outside of the acceptance range of +/−20% versus the target are deemed unacceptable and do no meet release criteria, which results in a pass/reject decision for each piece where the rejected pieces are dropped into a reject chute for further evaluation while all others proceed normally.

TABLE 6

Signature array counts correlate with proper mixing of a coating

| | Mean Ratio | Mean Total Count | Signature ID | Meets Release Criteria |
|---|---|---|---|---|
| °C. = T1 | | | | |
| Trial 1 | ~0 | ~100% Expected | Incorrect | No |
| Trial 2 | ~0.5 | ~100% Expected | Incorrect | No |
| Trial 3 | ~0.75 | ~100% Expected | Incorrect | No |
| Trial 4 | ~0.875 | ~100% Expected | ~Correct | Yes |
| Trial 5 | ~1.0 | ~100% Expected | Correct | Yes |
| Trial 6 | ~1.125 | ~100% Expected | ~Correct | Yes |
| Trial 7 | ~1.25 | ~100% Expected | Incorrect | No |
| Trial 8 | ~1.5 | ~100% Expected | Incorrect | No |
| °C. = T2 | | | | |
| Trial 1 | ~0 | ~50% Expected | Incorrect | No |
| Trial 2 | ~0.5 | ~50% Expected | Incorrect | No |
| Trial 3 | ~0.75 | ~50% Expected | Incorrect | No |
| Trial 4 | ~0.875 | ~50% Expected | ~Correct | No |
| Trial 5 | ~1.0 | ~50% Expected | Correct | No |
| Trial 6 | ~1.125 | ~50% Expected | ~Correct | No |
| Trial 7 | ~1.25 | ~50% Expected | Incorrect | No |
| Trial 8 | ~1.5 | ~50% Expected | Incorrect | No |

Those of ordinary skill in the art of pharmaceutical sciences recognize that a similar method as that described in this Example 3 may be employed for quality control and release testing of many mixtures used to coat solid supports of many types. Additionally, it is evident to the skilled practitioner that this Example 3 allows for the methods of this invention to substitute for other costly and or more complicated analytical methods that might otherwise be used to assure proper mixing of formulation components and subsequent coating of supports with those mixtures. Also, the method of the present invention can be performed "in-line" thereby allowing for real time monitoring of the coating process, thereby avoiding the manufactured batch being placed on hold awaiting release results, and should a problem be identified, the entire batch is not affected.

EXAMPLE 4

Uniformity of a Detected Code Indicates Uniform Coating of Components that are Deposited on a Hemostatic Sponge This Example illustrates a process for making a product using attributes of the signature array of the present invention to detect uniform coating of components to be deposited on a solid matrix of a product, while maintaining all of the benefits that said array has for authenticating the product. Particularly, this also demonstrates a process that would be useful for manufacturing a hemostatic sponge.

A hemostatic sponge is as described in Example 3, above, and product release is dependent upon uniform coating of the support after removal from the immersion and drying. To simulate both the proper manufacturing process and potential errors of non-uniform coating in manufacture, a constant volume of Portion A was mixed with Portion B in the correct 9:1 ratio as shown for Trial 5 of Table 5 in Example 3. In accordance with proper manufacturing process, three replicate coatings were achieved by fully immersing a single solid matrix support in each replicate case for a fixed time (T1) and at a temperature such that the required amount of the labeled Portion A/Portion B suspension is adhered at specified density to the support surface. To simulate a manufacturing deficiency, three replicate coatings were achieved by fully immersing a single solid matrix support time T1/4, then withdrawing the support ¼ its length for each increment of the following increments, T1/4. Thus, the first ¼ of the support has been immersed for T1×0.25, the second ¼ for T1×0.50, the third ¼ for T1×0.75 m and the final ¼ of the support for the full duration of T1.

To simulate quality control and release testing of the coated solid supports, the total microparticle counts and the membership within microparticle clusters was determined for each ¼ of the support area, and results are shown in Table 7.

TABLE 7

Signature array counts correlate with the uniformity of a coating

| Immersion | Mean Total Count | Meets Release Criteria |
|---|---|---|
| Full | | |
| 1st ¼ | ~100% Expected | |
| 2nd ¼ | ~100% Expected | |
| 3rd ¼ | ~100% Expected | |
| 4th ¼ | ~100% Expected | Yes |
| By ¼ | | |
| 1st ¼ | ~25% Expected | |
| 2nd ¼ | ~50% Expected | |
| 3rd ¼ | ~75% Expected | |
| 4th ¼ | ~100% Expected | No |

Those of ordinary skill in the art recognize that a similar method as that described in this Example may be employed for quality control and release testing of many mixtures used to coat solid supports of many types. Additionally, it is evident to the skilled practitioner that this Example allows for the methods of this invention to substitute for other costly and or more complicated analytical methods that might otherwise be used to assure uniform coating of supports. Also, the method of the present invention can be performed "in-line" thereby allowing for real time monitoring of the coating process, thereby avoiding that manufactured batch be placed on hold awaiting release results, and should a problem be identified, the entire batch is not affected.

EXAMPLE 5

Using Microparticulate Taggants Having Different Detectable Physical Properties to Assure that Product Contents' Match Product's Labels The present invention also relates to a method for using microparticulate taggants having different detectable physical properties to assure that product contents' match product's label, wherein each combination of properties is used as an encoding bit to create codes. The present invention thus further extends the utility of using the count or relative count of microparticles or symbols to create an authentication code in order to minimize the occurrence of packaging mismatch errors by providing a coding system that can be incorporated into product contents, into or onto product packaging containers, and into or onto product labels. The coding system provides for multiple checkpoints to assure against mix-up errors.

Figure 5:
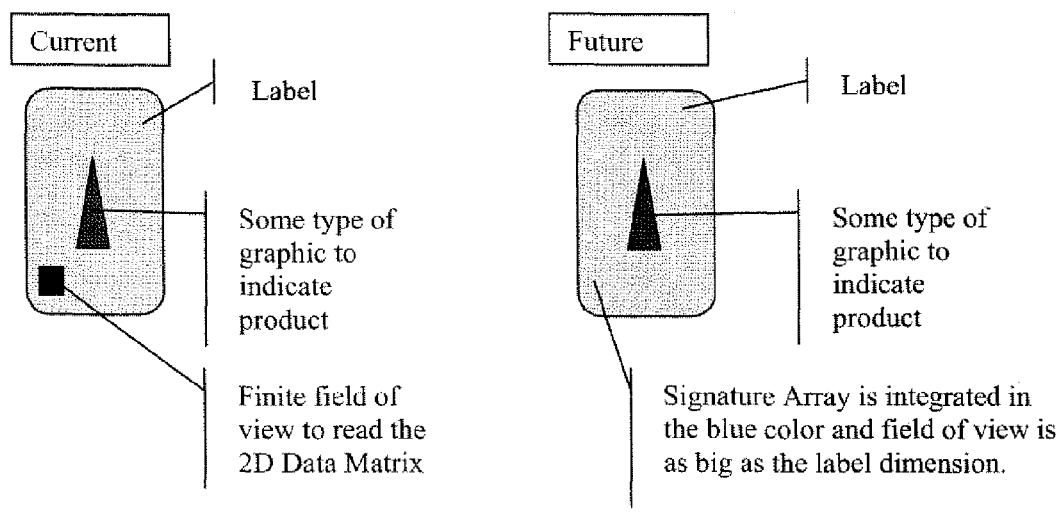
FIG. 5 is a schematic illustrating that label with signature array enables a much larger field of view and optimizes the scanning capabilities as well as diminishing the complexity of graphic design on locating the code at a specific position due to a specific production line characteristic.

FIG. 5 is a schematic illustrating that label with signature array enables a much larger field of view and optimizes the scanning capabilities as well as diminishing the complexity of graphic design on locating the code at a specific position due to a specific production line characteristic.

One advantage of this method is that the signature array can be used on all the components of the product and assure the entire integrity of all product components once assembled. Take for example all the components for a bottle of shampoo: the bottle, the lid, the front label and back label as well as the liquid shampoo could each have an individual signature array (or logically-linked set of signature arrays) and be individually scanned, at different sections of a production line, to ensure product integrity for each individual product assembly. Thus, each of the finished product's components has an integrated, "personalized" signature, such that more cumbersome procedures like scanning the box containing lids, the box containing the bottle, as well as the tote of shampoo are no longer necessary to assure the right components prior to beginning assembly of these components in production. The methods of the present invention avoid a mix-ups that are otherwise difficult to capture in production and could lead to the wrong product reaching the consumer.

Figure 6:
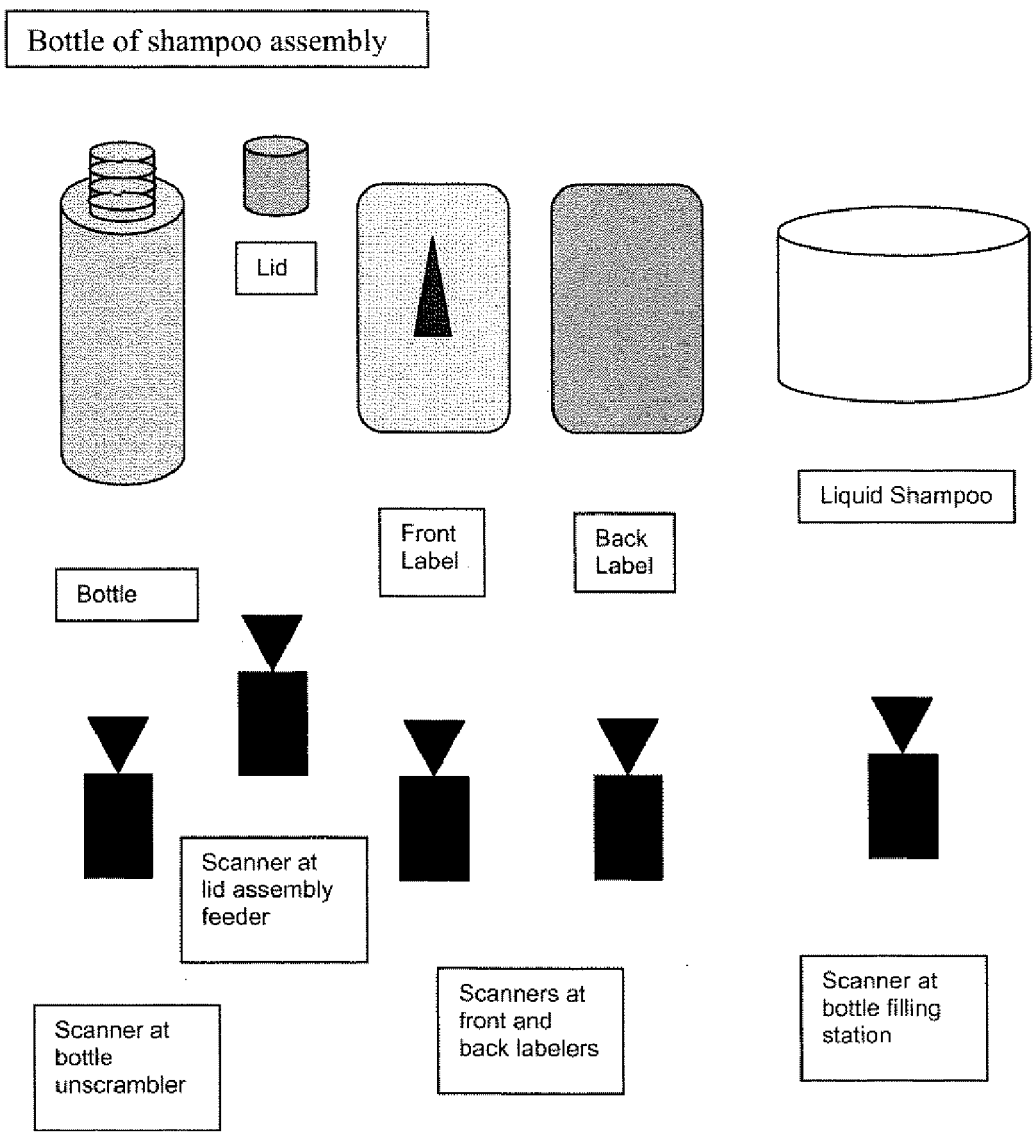
FIG. 6 is a schematic illustrating that all components of the product assembly are readable and can be scanned on production line on an individual basis to insure full product integrity for each product.

As shown in FIG. 6, all components of the product assembly are readable and can be scanned on production line on an individual basis to insure full product integrity for each product.

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All references are hereby incorporated into this application in their entirety.

EXAMPLE 6

Using Printed Symbol Taggants and a Tracer that Changes in Response to Exposure of the Product to an Environmental Stimulus as an Element of a Product Authentication Code The present invention also relates to a method for assuring the proper handling of a product, whether in the manufacturing process or after supply and distribution of the article. In this Example, a tracer which may be one or more elements of a product authentication code used to assure manufacturing processes undergoes a detectable change after exposure to environmental factors, such as high or low temperature thresholds, humidity, or radiation exposure.

In the present Example, labels are printed to be affixed top a medical device prior to steam sterilization, wherein the labels bear a responsive signature array element to assure exposure to steam temperature adequate for sterilization. Multiple sets of distinct populations of printable symbols are generated and selected for printing using flexographic digital printing. As shown in Table 8, five conventional characters ("T", "&", "J", "7", and "M") are indexed for printing in one of three indexed different fonts (normal, bold, or italic) and one of three indexed distinguishable styles (normal, strikethrough, or underscore) to create 45 (5×3×3) distinct clusters that can be used to create populations of printed symbols for product authentication. In order for the array to have an environmentally responsive element, all bold characters are printed on white labels using Sun Chemicals ThermaFLAG StS AIC23019, which changes from white to black upon exposure of the printed ink to a steam environment adequate to affect sterilization article bearing the label.

TABLE 8

Indexing of the 5 conventional characters, the 3 distinguishable fonts, and the 3 identifiable styles

| Character | | Font | | Style | |
|---|---|---|---|---|---|
| Index | Type | Index | Type | Index | Type |
| 1 | T | 1 | Normal | 1 | Normal |
| 2 | & | 2 | Bold | 2 | Strikethrough |
| 3 | J | 3 | Italic | 3 | Underline |
| 4 | 7 | | | | |
| 5 | M | | | | |

Characters of a signature array were selected using an algorithm written in MICROSOFT EXCEL spreadsheet that generated a population of heterogeneous printed symbols as a string, as follows. A look-up table was constructed for the 45 clusters of printed symbols, i.e., all possible combinations of Character×Font×Style, expressed as index position. The corresponding character was incorporated into the look-up table, corresponding to cluster number, as shown in the first two columns of Table 9. A user-specified signature array was designated by randomly selecting particular clusters out of the 45 possible clusters and arbitrarily assigning a frequency of appearance in the specified array for each of the selected cluster. Three representative user-specified signature arrays were designated as shown in Table 9: Array 1, Array 2, and Array 3. For each of 10,000 cells in the spreadsheet, a random number (Random 1) with values between 0 and 1 was generated and multiplied by the number of clusters, then 0.5 was added to the result, and the net result rounded to yield a random cluster number between 1 and 45 (Selected Cluster). Then, a random number with values between 0 and 1 (Random 2) was generated and compared to the fractional frequency specified for the Selected Cluster. If Random 2 was less than said specified frequency, the character corresponding to the Selected Cluster was selected for printing. For example, if Random Number 2 was less than 0.2 in a case where Cluster 3 had been selected randomly from all clusters, "J" was selected for printing, otherwise a value "FALSE" was returned and no character selected; hence, 20% of the time, "J" would be selected when Cluster 3 was the Selected Cluster. If a Selected Cluster had a specified frequency 0, Random Number 2 was never less than 0 and a value "FALSE" was always returned and no character selected. With each recalculation of the spreadsheet, strings of approximately 200+ characters of each array were selected. Representative strings for each of the arrays are as follows:

Array 1
MJT *M*TMMT *M*&T &*M*TJTMMMMM &&-MJJM & MJTMTM &JT &&-MMMTM   &*M*JM &JJ &*M*J &M && JTMJJ &*M*JJMJ &*MM*MMJMMJM &*M*&MMMM *M*TJ & J &&-JJ &M *M*JTM &JJM *M*T &T *MM*JJ &JM &J *M*M *M*& JJ &TMJJMMJTT &&-JMT &J *M*JMJJMTJ &MTMTJJ *M* TT *M*&M *M*JMT *M*M &JJM &MJ &MMJ &M &JJTJJM & JMMJJT &MMJ . . .

Array 2
&&-MJMTM &&-M &MMTJM &MT &&&-MJ &*M* TM &TTMTM *M*J &&-M *M*J &TMTJTMM &MM *MM*& JT &TM &MJ &TMTJMTJJJ *M*MM *M*M &M &&-TJ *M*TM TM &MMJ &&&-MJTMM &JTJJJ &M *M*J &MTTMT TM &&-J &*M*&TMM &M &J   MMTMJTTM &MJ &&- TT *M*&JMTMM &M &MTMJJ &J &M *M*TMMT *M*&&-M MTMM &T &MJMJ *M*JM &&-J &*M*MMT &J *M*&TJT & T &MMTTT &&&-. . .

Array 3
7 *J*7 *J*J&T7T&77& *F*7JMT77JJ7 *JFFF*TMT7T77777T 7J *J*T777&&&7JT7&JT&T   7777& *JF*7 *F*77T&TT&M *F* T& *J*T *F*777 *F*T7T7J& *FFJ*&T7J *F*777T&&&77& *F* 7 *J*J& *J*J *J*7T777M&7 *J*7TJ&T77&&T *F*M *J*T& *F*7 *F*77 TT *J*&77 *FF*M *J*T *J*M7777J7 *F*7 *J*& *J*M *J*M77T77JM 77 *J*& *FJ*TT77&7 *F*TJ&T *F*&7 *F*T7 . . .

Prior to sterilization, bold characters are missing from the array and there is no correlation between specified and observed character frequency for each of the three representative signature arrays. However, after exposure of the labels to a steam sterilization environment, bold characters appear and there is a close correlation between specified and observed character frequency for each of the three representative signature arrays.

Those of ordinary skill in the art of the present invention recognize that the clusters of printable symbols of the present invention are not limited to the representative characters, fonts, or styles shown in Table 5. For example, symbols like ✱, ■, ▲, ●, ✦, symbols or Greek alphabet characters or others can replace the Roman alphabet characters used in this example. Whole words or logos may replace or be used with individual characters or symbols in any index position. Color, grayscale level, font size, highlighting or the like can replace or be used with the fonts and styles used in this example. It is apparent that a variety of distinct clusters, by no means limited to the 45 clusters illustrated in Table 7, can be constructed from combinations of the forgoing discretely measurable common properties for the printed symbols.

A skilled practitioner recognizes that printing a code of the present invention is not limited to a label. A variety of other suitable surfaces for printing said code can be found on product packages, shrink wrap, containers (such as the vials or prepackaged syringes), on medical devices (such as in the coating of stents or on the casing of implantable defibrillators).

What is claimed is:

1. A method of authenticating a coated product, comprising the steps of: a) associating a population of entities with the product, wherein the population comprises at least two distinct clusters of entities having detectable absolute counts or relative counts of entities per cluster; b) assigning a signature array of the population of entities to the product as a product authentication code, wherein the signature array comprises information about the absolute counts or relative counts of entities of at least two distinct clusters of entities within the population; wherein information about the signature array and the product authentication code is recorded and wherein absolute count is the count or number measured in all or a portion of said coated product and relative count is a ratio between two or more absolute counts; c) analyzing the product to obtain a measured signature array of the population of entities associated with the product; d) comparing the measured signature array with that which is expected based on the recorded information; and e) accepting the product as authenticated when the measured signature array matches that which is expected.

2. The method of claim 1, wherein recorded information about the product is selected from the amount, concentration, or presence or absence of a product component.

3. The method of claim 1, wherein each of the at least two distinct clusters of entities has one or more discretely measurable common properties that are shared by entities within said cluster, but not by entities within any other cluster.

4. The method of claim 3, wherein the one or more discretely measurable common properties are properties of one or more tags associated with the entities.

5. The method of claim 4, wherein the one or more tags associated with the entities is selected from the group consisting of: colors, fluorescent dyes, ultraviolet radiation dyes, luminescent compositions, microparticles, haptens, nucleotides, polypeptides, scents, and a combination thereof.

6. The method of claim 3, wherein the one or more discretely measurable common properties of the entities are the size of the entities, the style of the entities, or the shape of the entities.

7. The method of claim 1, wherein the population of entities comprises microparticles.

8. The method of claim 7, wherein the microparticles are labeled with at least two discretely measurable fluorescent dyes.

9. The method of claim 8, wherein the at least two discretely measurable fluorescent dyes are present on the same microparticle.

10. The method of claim 8, wherein the microparticles are labeled with a fluorescent dye in at least two detectable different intensity levels.

11. The method of claim 1, wherein the population of entities comprises one or more types of entities selected from the group consisting of microparticles, nucleic acid molecules, peptides, polypeptides, hapten, or a combination thereof.

12. The method of claim 1, wherein during the step of associating a population of entities with the product, the population is associated with the product by incorporation on or in the coating medium of the product.

13. The method of claim 1, wherein the product is a solid pharmaceutical product.

14. The method of claim 1, wherein the entities are bioabsorbable and non-toxic in amounts used.

15. The method of claim 13, wherein the product is a medical device or a consumer product.

16. A method for quality control and release of products from a manufacturing process, comprising the steps of: a) associating a population of entities with a product during the manufacturing process, wherein the population of entities comprises at least two distinct clusters of entities having detectable absolute counts or relative counts of entities per cluster, wherein a signature array that comprises information about the absolute counts or relative counts of entities of the at least two distinct clusters of entities is recorded and wherein absolute count is the count or number measured in all or a portion of said product thereof and relative count is a ratio between two or more absolute counts; b) analyzing the product to obtain a measured signature array of the population of entities associated with the product; c) comparing the measured signature array with that which is expected based on the recorded information; and d) releasing products manufactured by the manufacturing process when the measured signature array matches that which is expected.

17. The method of claim 16, wherein recorded information about the product is selected from the amount, concentration, or presence or absence of a product component.

18. The method of claim 16, wherein each of the at least two distinct clusters of entities has one or more discretely measurable common properties that are shared by entities within said cluster, but not by entities within any other cluster.

19. The method of claim 16, wherein the one or more discretely measurable common properties are properties of one or more tags associated with the entities.

20. The method of claim 19, wherein the one or more tags associated with the entities is selected from the group consisting of: colors, fluorescent dyes, ultraviolet radiation dyes, luminescent compositions, microparticles, haptens, nucleotides, polypeptides, scents, and a combination thereof.

21. The method of claim 16, wherein the one or more discretely measurable common properties of the entities are the size of the entities, the style of the entities, or the shape of the entities.

22. The method of claim 16, wherein the population of entities comprises microparticles.

23. The method of claim 22, wherein the microparticles are labeled with at least two discretely measurable fluorescent dyes.

24. The method of claim 23, wherein the at least two discretely measurable fluorescent dyes are present on the same microparticle.

25. The method of claim 24, wherein the microparticles are labeled with a fluorescent dye in at least two detectable different intensity levels.

26. The method of claim 16, wherein the population of entities comprises one or more types of entities selected from the group consisting of microparticles, nucleic acid molecules, peptides, polypeptides, hapten, or a combination thereof.

27. The method of claim 16, wherein during the step of associating a population of entities with the product, the population is associated with the product by incorporation on or in the coating medium of the product.

28. The method of claim 16, wherein the product is a solid pharmaceutical product.

29. The method of claim 16, wherein the entities are bioabsorbable and non-toxic in amounts used.

30. The method of claim 16, wherein the product is a medical device or a consumer product.

31. A method for assuring the proper handling of a product comprising the steps of: a) associating a population of entities with a product during a manufacturing process, wherein the population of entities comprises at least two distinct clusters of entities having detectable absolute counts or relative counts of entities per cluster and wherein the absolute counts or relative counts of entities within at least one of said clusters changes in response to exposure of the product to an environmental stimulus and wherein absolute count is the count or number measured in all or portion of said product and relative count is a ratio between two or more absolute counts; b) analyzing the product to obtain a measured value of the counts of said cluster(s) that change(s) in response to exposure of the product to an environmental stimulus; c) comparing the measured counts with a corresponding expected counts acceptance value; and d) releasing products manufactured by the manufacturing process when the measured value is within an acceptable range of the expected value.

32. The method of claim 31, wherein the environmental stimulus is a maximum acceptable temperature, a minimum acceptable temperature, a maximum acceptable humidity, a minimum acceptable humidity, or a maximum acceptable level of electromagnetic radiation.

33. The method of claim 31, wherein each of the at least two distinct clusters of entities has one or more discretely measurable common properties that are shared by entities within said cluster, but not by entities within any other cluster.

34. The method of claim 31, wherein the one or more discretely measurable common properties are properties of one or more tags associated with the entities.

35. The method of claim 31, wherein the one or more tags associated with the entities is selected from the group consisting of: colors, fluorescent dyes, ultraviolet radiation dyes, luminescent compositions, microparticles, haptens, nucleotides, polypeptides, scents, and a combination thereof.

36. The method of claim 31, wherein the one or more discretely measurable common properties of the entities are the size of the entities, the style of the entities, or the shape of the entities.

37. The method of claim 31, wherein the population of entities comprises microparticles.

38. The method of claim 37, wherein the microparticles are labeled with at least two discretely measurable fluorescent dyes.

39. The method of claim 38, wherein the at least two discretely measurable fluorescent dyes are present on the same microparticle.

40. The method of claim 38, wherein the microparticles are labeled with a fluorescent dye in at least two detectable different intensity levels.

41. The method of claim 31, wherein the population of entities comprises one or more types of entities selected from the group consisting of microparticles, nucleic acid molecules, peptides, polypeptides, hapten, or a combination thereof.

42. The method of claim 31, wherein during the step of associating a population of entities with the product, the population is associated with the product by incorporation on or in the coating medium of the product.

43. The method of claim 31, wherein the product is a solid pharmaceutical product.

44. The method of claim 31, wherein the entities are bioabsorbable and non-toxic in amounts used.

45. The method of claim 31, wherein the product is a medical device or a consumer product.

46. A method for minimizing the occurrence of packaging mismatch errors comprising the steps of: a) associating a population of entities with a product label to be applied to a container during a manufacturing process, wherein the population of entities comprises at least two distinct clusters of entities having detectable absolute counts or relative counts of entities per cluster, wherein a signature array that comprises information about the absolute counts or relative counts of entities of the at least two distinct clusters of entities is recorded and wherein absolute count is the count or number measured in all or portion of said product and relative count is a ratio between two or more absolute counts; b) determining that the signature array is consistent with proper match between the label and the container; and c) rejecting labeled containers that are determined to be mismatched.

47. The method of claim 46 further comprising the step of performing steps b and c in-line during a manufacturing labeling operation.

48. The method of claim 46, wherein the container also incorporates a signature array for matching with the signature array of the label.

49. The method of claim 46, wherein the container and or the label further comprises machine-readable features for matching with any or all signature arrays.

50. The method of claim 49, wherein the machine-readable feature is a bar code.

51. The method of claim 46, wherein each of the at least two distinct clusters of entities has one or more discretely measurable common properties that are shared by entities within said cluster, but not by entities within any other cluster.

52. The method of claim 51, wherein the one or more discretely measurable common properties are properties of one or more tags associated with the entities.

53. The method of claim 52, wherein the one or more tags associated with the entities is selected from the group consisting of: colors, fluorescent dyes, ultraviolet radiation dyes, luminescent compositions, microparticles, haptens, nucleotides, polypeptides, scents, and a combination thereof.

54. The method of claim 46, wherein the one or more discretely measurable common properties of the entities are the size of the entities, the style of the entities, or the shape of the entities.

55. The method of claim 46, wherein the population of entities comprises microparticles.

56. The method of claim 55, wherein the microparticles are labeled with at least two discretely measurable fluorescent dyes.

57. The method of claim 56, wherein the at least two discretely measurable fluorescent dyes are present on the same microparticle.

58. The method of claim 57, wherein the microparticles are labeled with a fluorescent dye in at least two detectable different intensity levels.

59. The method of claim 46, wherein the population of entities comprises one or more types of entities selected from the group consisting of microparticles, nucleic acid molecules, peptides, polypeptides, hapten, or a combination thereof.

60. The method of claim 46, wherein the product is a medical device, a pharmaceutical product or a consumer product.

61. The method of claim 46, wherein the entities are bioabsorbable and non-toxic in amounts used.

62. The method of claim 46, further comprising the steps of:
a) associating the signature array with the bulk of a product prior to filling the labeled containers;
b) determining whether or not the signature array is consistent with proper match between the product bulk and the container; and
c) rejecting filled containers for which the signature array is determined not to be consistent with proper match between the label and the container.

63. The method of claim 62 further comprising the step of performing steps b and c in-line during a manufacturing labeling operation.

64. The method of claim 62, wherein the container and or the label further comprises machine-readable features for matching with any or all signature arrays.

65. The method of claim 62, wherein the machine-readable feature is a bar code.

66. The method of claim 62, wherein each of the at least two distinct clusters of entities has one or more discretely measurable common properties that are shared by entities within said cluster, but not by entities within any other cluster.

67. The method of claim 66, wherein the one or more discretely measurable common properties are properties of one or more tags associated with the entities.

68. The method of claim 67, wherein the one or more tags associated with the entities is selected from the group consisting of: colors, fluorescent dyes, ultraviolet radiation dyes, luminescent compositions, microparticles, haptens, nucleotides, polypeptides, scents, and a combination thereof.

69. The method of claim 66, wherein the one or more discretely measurable common properties of the entities are the size of the entities, the style of the entities, or the shape of the entities.

70. The method of claim 62, wherein the population of entities comprises microparticles.

71. The method of claim 70, wherein the microparticles are labeled with at least two discretely measurable fluorescent dyes.

72. The method of claim 71, wherein the at least two discretely measurable fluorescent dyes are present on the same microparticle.

73. The method of claim 71, wherein the microparticles are labeled with a fluorescent dye in at least two detectable different intensity levels.

74. The method of claim 62, wherein the population of entities comprises one or more types of entities selected from the group consisting of microparticles, nucleic acid molecules, peptides, polypeptides, hapten, or a combination thereof.

75. The method of claim 62, wherein the product is a medical device, a pharmaceutical product, or a consumer product.

76. The method of claim 62, wherein the entities are bioabsorbable and non-toxic in amounts used.

* * * * *